(12) United States Patent
Pillai et al.

(10) Patent No.: US 7,351,389 B2
(45) Date of Patent: *Apr. 1, 2008

(54) AMINOCARBOXYLATE LIGANDS HAVING SUBSTITUTED AROMATIC AMIDE MOIETIES

(75) Inventors: Radhakrishna K. Pillai, Kendall Park, NJ (US); Sang I. Kang, Cranbury, NJ (US); Edmund R. Marinelli, Lawrenceville, NJ (US); Ramachandran S. Ranganathan, Princeton, NJ (US); Michael F. Tweedle, Princeton, NJ (US)

(73) Assignee: Bracco International B.V., Amsterdam (NL)

( * ) Notice: Subject to any disclaimer, the term of this patent is extended or adjusted under 35 U.S.C. 154(b) by 270 days.

This patent is subject to a terminal disclaimer.

(21) Appl. No.: 10/963,708

(22) Filed: Oct. 13, 2004

(65) Prior Publication Data

US 2005/0090689 A1 Apr. 28, 2005

Related U.S. Application Data

(60) Continuation of application No. 10/042,721, filed on May 29, 2002, now Pat. No. 6,875,864, which is a continuation of application No. 08/471,556, filed on Jun. 6, 1995, now abandoned, which is a division of application No. 08/010,909, filed on Jan. 29, 1993, now abandoned, which is a continuation-in-part of application No. 07/738,998, filed on Aug. 1, 1991, now abandoned.

(51) Int. Cl.
  *C07C 231/02* (2006.01)
  *C07D 257/00* (2006.01)

(52) U.S. Cl. .............. 423/366; 424/9.363; 534/16; 540/465; 540/474; 564/27; 564/340; 564/372; 564/374; 564/440

(58) Field of Classification Search ........... 540/474; 534/16
See application file for complete search history.

(56) References Cited

U.S. PATENT DOCUMENTS

| | | | |
|---|---|---|---|
| 4,631,337 A | 12/1986 | Tomalia et al. | |
| 4,647,447 A | 3/1987 | Gries et al. | |
| 4,687,659 A | 8/1987 | Quay | |
| 4,859,451 A | 8/1989 | Quay et al. | |
| 4,885,363 A | 12/1989 | Tweedle et al. | |
| 4,899,755 A | 2/1990 | Lauffer et al. | |
| 4,957,939 A | 9/1990 | Gries et al. | |
| 4,963,344 A | 10/1990 | Gries et al. | |
| 4,983,376 A | 1/1991 | Sherry | |
| 5,021,236 A | 6/1991 | Gries et al. | |
| 5,573,752 A | 11/1996 | Ranganathan et al. | |
| 5,639,879 A | 6/1997 | Mease et al. | |
| 6,875,864 B2* | 4/2005 | Pillai et al. ............... 540/474 |
| 2002/0127629 A1 | 9/2002 | Bogdanov et al. | |

FOREIGN PATENT DOCUMENTS

| | | |
|---|---|---|
| AU | 78995/87 | 3/1988 |
| AU | 31485/89 | 9/1989 |
| AU | 61073/90 | 2/1991 |
| CA | 2039846 | 10/1991 |
| EP | 0230893 | 8/1987 |
| EP | 0325762 | 8/1989 |
| EP | 450742 | 10/1991 |
| NZ | 227421 | 10/1990 |
| WO | WO89/05802 | 6/1989 |
| WO | WO/92/04336 | 3/1992 |

OTHER PUBLICATIONS

Villringer et al., "Dynamic Imaging with Lanthanide Chelates in Normal Brain: Contrast Due to Magnetic Susceptibility Effects", Magnetic Resonance in Medicine. 6. 164-174 (1988).

Shehadi, "Contrast Media Adverse Reactions: Occurrence, Recurrence, and Distribution Patterns", Diagnostic Radiology, vol. 143, No. 1, pp. 11-17 (Ann 1982).

Bettmann, "Angiographic Contrast Agents: Conventional and New Media Compared". AJE. 139, pp. 787-794 (Oct. 1982).

Bettmann et al., "Recent Advances in Contrast Agents", Radiologic Clinics of North America. vol. 24, No. 3, pp. 347-357 (Sep. 1986).

Wedeking et al., "Comparison of the Biodistribution of $^{153}$Gd-Labeled Gd(DTPA)2-, Gd(DOTA)" and Gd(Acetate)n in Mice, Mud. Med. Biol., vol. 15, No. 4. nn. 395-402 (1988).

(Continued)

Primary Examiner—Robert Sellers
(74) Attorney, Agent, or Firm—Kramer Levin Naftalis & Frankel LLP

(57) ABSTRACT

Novel metal-chelate complexes comprising aminocarboxylate ligands including substituted aromatic amide moieties, such as those having the formula

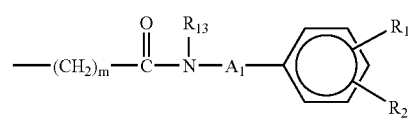

wherein $R_{13}$, $A_1$, $R_1$ and $R_2$ are as defined herein, are disclosed.

5 Claims, No Drawings

OTHER PUBLICATIONS

Tweedle et al., "Reaction of Gadolinium Chelates with Endogenously Available Tons". Magnetic Resonance Imaging. vol. 9. pp. 409-415 (1991).

Tweedle, "Work in Progress Toward Nonionic Macrocyclic Gadolinium(III) Complexes", in Contrast and Contrast Agents in Magnetic Resonance Imaging, edited by P. A. Rink, European Workshop on Magnetic Resonance in Medicine. pp. 65-73 (1989).

Brechbiel et at., "Synthesis of 1.(p-Isothiocyanatobenzyl) Derivatives of DTPA and EDTA. Antibody Labeling and Tumor-Imaging Studies", Inorg. Chem., 25, pp. 2772-2781 (1986).

Hoey et al., "Chemistry of X-ray Contrast Media", Handbook of Experimental Pharmpcology. n. 23-125 (1984).

Wedeking et al,, "Biodistribution and Excretion of New Gd-Complexes in Mice", p. 801 and Multi-Tissue Pharmacokinetic Evaluation of MRI Contrast Agents; p. 802, Society of Magnetic Resonance in Medicine, 8th Annual Meeting, The RAI Consrescentrum. Amsterdam. The Netherlands (Aug. 12-18, 1989).

Cavagna et a!. , "Biliary Agents: New Formulations", International Symposium & Course, Liver Imaging—Present and Future in MRI, CT & US, Harvard Medical School—Boston. Massachusetts, 3 pages (Jun. 25-27, 19901).

Broan et at., "Structure and solution stability of indium and gallium complexes of 1,4,7-triazacyclononanetriacetate and yttrium complexes of 1,4,7,10-tetra-azacyclododecanetetracetate and related ligands . . . ", J. Chem. Soc., Perkin Trans. 2.No. 1. pp. 87-99(1991).

Dischino et al., "Synthesis of Nonionic Gadolinium Chelates Useful as Contrast Agents for Magnetic Resonance Imaging", Inorganic Chemistry, vol. 30, No. 6, p. 1265-1269 (1991).

Wedeking et al., "Society of Magnetic Resonance in Medicine", Book of Abstracts, 8th Annual Meeting, pp. 801-802, Aug. 12-18, 1989.

Society of Magnetic Resonance in Medicine, Book of Abstracts, 8th Annual Meeting, Aug. 12-18, 1989.

* cited by examiner

AMINOCARBOXYLATE LIGANDS HAVING SUBSTITUTED AROMATIC AMIDE MOIETIES

This application is a continuation of U.S. application Ser. No. 10/042,721 filed May 29, 2002, now U.S. Pat. No. 6,875,864, which is a continuation of U.S. application Ser. No. 08/471,556, filed Jun. 6, 1995, now abandoned, which is a divisional of U.S. application Ser. No. 08/010,909, filed Jan. 29, 1993, now abandoned, which is a continuation-in-part of U.S. application Ser. No. 07/738,998, filed Aug. 1, 1991, now abandoned. All of these applications are hereby incorporated by reference in their entirety.

BACKGROUND OF THE INVENTION

Metal-chelating ligands are useful in diagnostic medicine as contrast agents. X-ray imaging, radionuclide imaging, ultrasound imaging and magnetic resonance imaging can each be enhanced by the use of a metal atom bound to a chelating ligand. For example, a chelating ligand can become a radiopharmaceutical when it is prepared as a chelate complex with $^{99m}$Tc, $^{111}$In, $^{67}$Ga, $^{140}$La, $^{169}$Yb, $^{68}$Ga, $^{90}$Y, $^{188}$Re, $^{153}$Sm or other radioactive metal ions. When a chelating ligand is complexed with the stable isotopes of the lanthanides, tantalum, bismuth or other elements with molecular weight higher than iodine, the resulting complex absorbs x-rays sufficiently to act as an x-ray contrast agent. In some cases, the agents that are useful in x-ray imaging absorb, reflect or scatter ultrasound radiation sufficiently to be used as an ultrasound agent. If a chelating ligand is complexed with a paramagnetic metal atom that has a symmetric electronic ground state (e.g., $Gd^{+3}$, and octahedral $Mn^{+2}$, $Fe^{+3}$, $Cr^{+3}$) the resulting complex will be useful as a spin relaxation catalyst that is used in magnetic resonance imaging (also known as NMR imaging) as a contrast agent. If a chelating agent is complexed with a paramagnetic metal atom that has an unsymmetrical electronic ground state (e.g., dysprosium(III), holmium(III) and erbium(III), the resulting complex will be useful as a chemical shift agent in magnetic resonance imaging or in magnetic resonance in vivo spectroscopy. In addition, any paramagnetic metal ion complex may be used as a contrast agent by virtue of its magnetic susceptibility as disclosed by villringer et al. (*Magnetic Resonance in Medicine*, 6, 164-174, 1988).

The chelating ligands can also be bifunctional. That is, they can bind tightly to the metal ion forming a chelate while at the same time bearing a second functionality which confers upon it desirable chemical, physical and/or biological properties. Desirable physical properties of the chelator differ depending on the diagnostic or therapeutic purpose of the metal chelate. Desirable physical properties common to all uses are high affinity for the metal ion bound to the chelator, and ease of synthesis. When it is desired to use the metal chelate as a contrast medium for NMR imaging or general purpose x-ray imaging, the desirable physical properties are high water solubility, high chemical stability and viscosity and osmolality of a formulated drug solution as close as possible to those of human blood. Further, in the specific instance of a spin relaxation catalyst, the greatest possible relaxivity is desired. Relaxivity as used herein is understood to be as the effectiveness, per mole of complex, of altering the relaxation times of the nuclei being imaged.

Human blood has an osmolality of 0.3 Osmol/kg-water. Hyperosmolality is a well known contributor to adverse patient reactions to injected contrast media, and the lower osmolality of newer x-ray agents is due to their being nonionic molecules (possessing a net zero overall charge) (Shehadi, W. H.; "Contrast media adverse reactions: occurrence, reoccurrence and distribution patterns", *Radiol*, 1982, 143, 11-17. Bettman, M. A.; "Angiographic contrast agents; conventional and new media compared", *Am. J. Roentgen*, 1982, 139, 787-794. Bettman, M. A. and Morris, T. W.; Recent advances in contrast agents, *Radiol. Clin. North Am.*, 1986, 24, 347-357.). Many gadolinium-based NMR agents in the prior art that are useful have a net negative overall charge, and therefore their aqueous formulated solutions have high osmolality. For example, $Gd(DTPA)^{2-}$ where DTPA stands for diethylenetriaminepentaacetic acid is formulated for use at 0.5M in water as the N-methylglucamine salt. The osmolality of the solution is 1.6 to 2.0 Osmol/kg-water. New nonionic Gd complexes are described in U.S. Pat. Nos. 4,859,451 and 4,687,659. The preferred new gadolinium complexes of the present invention are nonionic—they are not salts. When these nonionic gadolinium complexes are formulated at 0.5M in water the osmolality of the solutions is 0.3-0.6 Osmol/kg-water. The complex should be generally inert to interaction with the body other than general tissue distribution and excretion, usually by the renal route, without, or minimally, depositing Gd metal in tissues for long periods of time. Gd complexes of macrocyclic aminocarboxylates are generally more chemically inert than Gd complexes of linear aminocarboxylates (P. Wedeking and M. Tweedle. *Nucl. Med. Biol.*, 15, 395-402, 1988; M. Tweedle et al., *Magn. Reson. Imog.*, 9, 409-415, 1991; and M. Tweedle, "Contrast and Contrast Agents in Magnetic Resonance Imaging", edited by P. A. Rink, *European Workshop on Magnetic Resonance in Medicine*, 1989) The preferred aminocarboxylate ligands for Gd are therefore members of the macrocyclic aminocarboxylate class, and are, in addition, nonionic. These properties are important to NMR imaging, but, in addition, the effectiveness of an agent for NMR imaging can be increased by altering the chemical structure so as to increase the ability of the metal chelate to affect the relaxation times of water protons.

In radiopharmaceutical imaging the doses administered are relatively small so that matching the drug formulation's physical properties to those of human blood is relatively unimportant. In this use biological specificity is more important. In particular, one could use $^{99m}$Tc as the metal and a chelating ligand which is functionalized with a biologically active entity such as a bile acid, fatty acid, amino acid, peptide, protein or one of numerous chemical entities known to bind receptors in vivo. NMR contrast media may also make use of biological specificity.

In radiopharmaceutical therapy, the metal ions may be chosen from among those known in the art; for example, $^{90}$Y, $^{188}$Re, $^{153}$Sm. For this purpose the chelating ligand is generally covalently bound to a disease specific entity such as monoclonal antibody. When the metal-chelator-antibody conjugate is injected into humans, it concentrates at the disease site, usually a malignant tumor. In this use the chelating ligand must contain a reactive functionality which allows for a covalent bond to be formed between the chelating ligand and the antibody. Important characteristics of the reactive functionality are as follows: (1) it must be covalently attached to the chelator such that it does not significantly diminish the affinity of the chelator for the metal ion; (2) it must allow simple synthesis in high yield of metal-chelator-antibody conjugates, the conjugate so-formed should have maximal affinity for its antigen, such affinity being minimally diminished as a result of covalently attaching the metal-chelator; (3) it should ideally allow for rapid excretion and/or optimal dosimetry of the radioactive metal chelator in the event that the metal-chelator-antibody conjugate is decomposed or metabolized in vivo.

When the metal is non-radioactive and paramagnetic such as gadolinium (III), the bifunctional chelate is useful in magnetic resonance imaging as a contrast agent, either as a discrete molecule or bound to substances such as lipids, sugars, alcohols, bile acids, fatty acids, receptor-binding ligands, amino acids, peptides, polypeptides, proteins, and monoclonal antibodies. When the metal is radioactive, such as yttrium(III) as $^{90}$Y, the bifunctional chelate is useful in labeling monoclonal antibodies for use in radiotherapy. When the metal is $^{99m}$Tc, $^{111}$In, $^{201}$Tl, $^{67}$Ga, $^{68}$Ga or the like, the chelate is useful in radiopharmaceutical imaging.

Two general methods have been employed for making bifunctional chelates from chelating agents. In the first method one or more carboxylic acid groups of a polyaminopolycarboxylic acid chelator are activated by conversion to such activating groups as internal or mixed anhydrides, activated esters (e.g., p-nitro phenyl, N-hydroxysuccinimide, etc.) or with other derivatives known to those skilled in the art. The activated acid group is then reacted with the protein. The metal ion is then added to the protein-chelator complex.

There are two problems with this method. First, using a potential donor group, the carboxylic acid, to react with the protein can diminish the strength of the chelate and contribute to the chemical lability of the metal ion. The second problem arises because the chelating ligands have several carboxylates that are not uniquely reactive. When the chelating ligand is combined with an activating agent more than one species can result because the number and chemical position of the groups activated cannot be adequately controlled. When a mixture of such variously activated chelating ligands is added to protein, protein-chelator complexes of variable and uncertain chelating strength can be formed. Also, multiple activation of carboxylic acids on a chelator leads to intra- and inter-molecular crosslinking which is a major source of decreased immunospecificity. This problem could be overcome by separating all of the products formed from the reaction of the activating agent with the chelating ligand, but that process is very laborious and makes the overall synthesis highly inefficient.

The second method for making a bifunctional chelate is to prepare a chelating ligand with a unique reactive function, such as an isothiocyanate, attached to the chelating ligand at a position that does not substantially diminish the strength with which the chelating ligand binds the metal ion. An article entitled "Synthesis of 1-(p-isothiocyanato-benzyl) derivatives of DTPA and EDTA, Antibody Labeling and Tumor-Imaging Studies" by Martin W. Brechbiel, Otto A. Gansow, Robert W. Atcher, Jeffrey Schlom, Jose Esteban, Diane E. Simpson, David Colcher, *Inorganic Chemistry*, 1986, 25, 2772 is illustrative of the above second method. Also, U.S. Pat. No. 4,885,363 describes these methods as they apply specifically to nonionic macrocyclic aminocarboxylates.

Wedeking et al., "Biodistribution and Excretion of New Gd-Complexes in Mice", Abstracts of the 8th Annual Meeting of the Society of Magnetic Resonance in Medicine, 801, 1989, have disclosed the compound

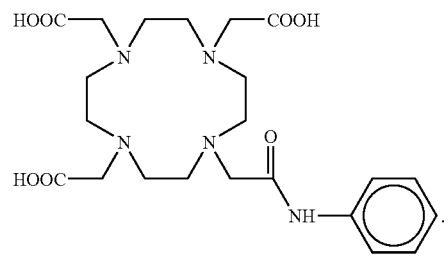

When used to chelate a paramagnetic ion, e.g., Gd, in magnetic resonance imaging, this compound was found to have poor water solubility, although acceptable relaxivity.

BRIEF DESCRIPTION OF THE INVENTION

It is an object of this invention to provide new metal-chelating ligands.

It is an object of this invention to provide new metal chelate complexes that are nonionic.

Another object is to provide metal chelating ligands which when complexed with a metal heavier than iodine (e.g., Ba, Ta, Pb, Bi, Lanthanides) are effective as x-ray contrast agents.

Another object is to provide metal chelating ligands which when complexed with gamma emitting radioactive nuclide (e.g., $^{99m}$Tc or $^{111}$In) are effective as imaging radiopharmaceuticals.

Another object is to provide metal chelating ligands which when complexed with beta or alpha emitting radioactive nuclide (e.g., $^{90}$Y, $^{153}$Sm, $^{188}$Re, $^{212}$Bi) are effective as therapeutic radiopharmaceuticals.

It is a further object of this invention to provide metal-chelating ligands whose metal chelate complexes in aqueous solution have low osmolality.

It is a further object of this invention to provide metal-chelating ligands whose metal chelate complexes have low acute toxicity.

It is a further object of this invention to provide metal-chelating ligands which, when complexed with a paramagnetic metal atom, are effective as relaxation catalysts in magnetic resonance imaging.

It is a further object of this invention to provide bifunctional metal-chelating ligands that have the ability to covalently bind to proteins or other biologically active molecules thereby imparting biological specificity to the metal chelate complex. The conversion of the novel molecules described herein to bifunctional chelates is accomplished using the methods described above.

It is a further object of this invention to provide new metal complexes with increased relaxivity.

It is a further object of this invention to provide bifunctional metal-chelating ligands that are thermodynamically stable, kinetically inert and, when desired, electrically neutral.

These, and other objects which will be appreciated by the practitioner of this invention, are achieved by substituting at one of the nitrogen atoms of an aminocarboxylate ligand a substituted aromatic amide moiety of the formula

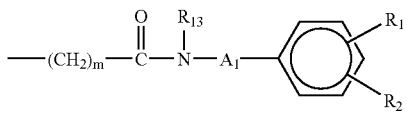

wherein $A_1$ is —$(CH_2)_{m'}$— or a single bond;

$(CH_2)_m$ and $(CH_2)_{m'}$ may independently be substituted with alkyl or hydroxyalkyl;

$R_{13}$ is hydrogen, alkyl, arylalkyl, aryl, alkoxy, hydroxyalkyl;

$R_1$ and $R_2$ are each independently hydrogen, alkyl, —$NO_2$, —$NH_2$,

NCS,

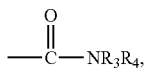

$NR_3COR_9$, where $R_9$ is alkyl or hydroxyalkyl, with the proviso that at least one of $R_1$ and $R_2$ must be other than hydrogen;

$R_3$ and $R_4$ are independently hydrogen, alkyl, arylalkyl, aryl, alkoxy and hydroxyalkyl;

$R_{12}$ is hydrogen, alkyl or hydroxyalkyl;

m and m' are independently 1 to 5;

and multimeric forms thereof.

Preferred are those compounds where $A_1$ is a single bond.

DETAILED DESCRIPTION OF THE INVENTION

The terms "alkyl" and "alkoxy" as used throughout the specification, refer to both straight and branched chain groups. Those groups having 1 to 5 carbon atoms are preferred and methyl is the most preferred alkyl group.

The term "aryl" as used throughout the specification refers to phenyl and substituted phenyl. Preferred substituted phenyl groups are those substituted with 1, 2 or 3 halogen, hydroxyl, hydroxyalkyl, alkyl, alkoxy, carbamoyl, carboxamide, acylamino or carboxyl groups.

Hydroxyalkyl refers to straight and branched alkyl bearing radicals R—OH groups such as —$CH_2CH_2OH$, —$CH_2CHOHCH_2OH$, $CH(CH_2OH)_2$ and the like. Such chemistry is well known to those skilled in the art (Sovak, M., editor, *Radiocontrast Agents,* Springer-Verlag, 1984, pp. 1-125).

As described above, aminocarboxylate nuclei known in the art can be provided with a substituted aromatic amide moiety of formula I to provide the novel compounds of the present invention.

Exemplary novel aminocarboxylates having a substituted aromatic amide moiety include compounds of the formula

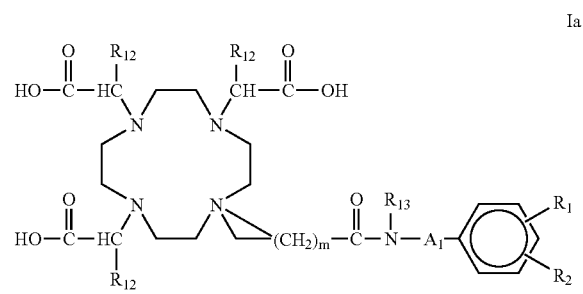

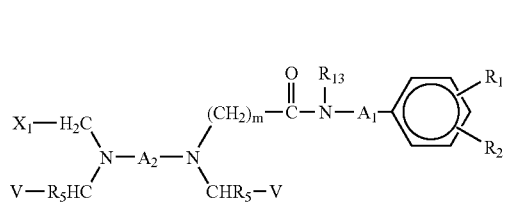

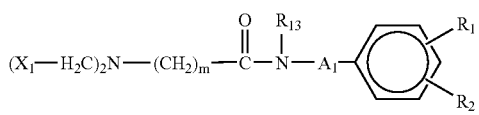

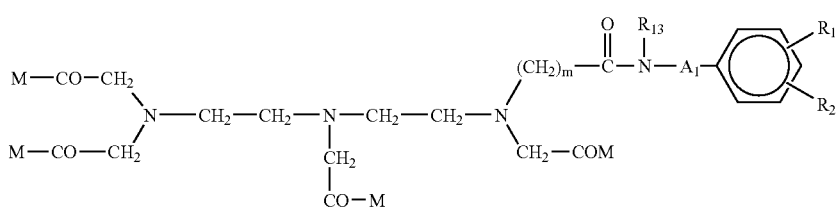

wherein in formulae Ia, Ib, Ic and Id, m, $R_{13}$, $A_1$, $R_1$, $R_2$ and $R_{12}$ are as defined above for formula I and further wherein $X_1$ is —$COOY_1$, $PO_3HY_1$ or —$CONHOY_1$;

$Y_1$ is a hydrogen atom, a metal ion equivalent and/or a physiologically biocompatible cation of an inorganic or organic base or amino acid;

$A_2$ is —$CHR_6$—$CHR_7$—, —$CH_2CH_2(ZCH_2$—$CH_2)_n$—,

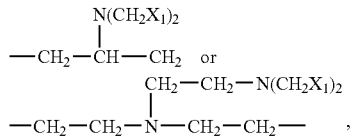

wherein $X_1$ is as defined above;

each $R_5$ is hydrogen or methyl;

$R_6$ and $R_7$ together represent a trimethylene group or a tetramethylene group or individually are hydrogen atoms, lower alkyl groups (e.g., 1-8 carbons), phenyl groups, benzyl groups or $R_6$ is a hydrogen atom and $R_7$ is —$(CH_2)_p$—$C_6H_4$—W-protein where p is 0 or 1, W is —NH—, —NH-$COCH_2$— or —NHCS—, protein represents a protein residue;

n is 1, 2 or 3;

Z is an oxygen atom or a sulfur atom or the group $NCH_2X_1$ or $NCH_2CH_2OR_8$ wherein $X_1$ is as defined above and $R_8$ is $C_{1-8}$alkyl;

V is $X_1$ or is —$CH_2OH$, —$CONH(CH_2)_rX_1$ or —COB, wherein $X_1$ is as defined above, B is a protein or lipid residue, r is an integer from 1 to 12, or if $R_5$, $R_6$ and $R_7$ are each hydrogen; then both V's together form the group

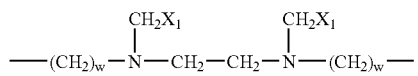

where $X_1$ is as above, w is 1, 2 or 3, provided that at least two of the substituents $Y_1$ represent metal ion equivalents of an element with an atomic number of 21 to 29, 42, 44 or 57 to 83; from 1 to 4, advantageously 2 or 3, and preferably 3 M's are —OH and the balance independently are —$OR_{10}$, —$NH_2$, —$NHR_{10}$ and/or $NR_{10}R_{10}'$ wherein $R_{10}$ and $R_{10}'$ are selected from an organic alkyl radical of up to 18 carbon atoms which may be substituted.

The compounds of formulae Ia, Ib, Ic and Id and salts thereof, can be complexed with a para-magnetic metal atom and used as relaxation enhancement agents for magnetic resonance imaging. These agents, when administered to a mammalian host (e.g., humans) distribute in various concentrations to different tissues, and catalyze relaxation of protons (in the tissues) that have been excited by the absorption of radiofrequency energy from a magnetic resonance imager. This acceleration of the rate of relaxation of the excited protons provides for an image of different contrast when the host is scanned with a magnetic resonance imager. The magnetic resonance imager is used to record images at various times generally before and after administration of the agents, and the differences in the images created by the agents' presence in tissues are used in diagnosis. In proton magnetic resonance imaging, paramagnetic metal atoms such as gadolinium(III), and octahedral manganese(II), chromium(III) and iron(III) (all are paramagnetic metal atoms with a symmetrical electronic configuration) are preferred as metals complexed by the ligands of formula I; gadolinium(III) is most preferred due to the fact that it has the highest paramagnetism, low toxicity, when complexed to a suitable ligand, and high lability of coordinated water.

The metal-chelating ligands of the present invention can be complexed with a lanthanide (atomic number 58 to 71) and used as chemical shift agents in magnetic resonance imaging or in magnetic resonance in vivo spectroscopy.

While the above-described uses for the metal-chelating ligands of the present invention are preferred, those working in the diagnostic arts will appreciate that the ligands can also be complexed with the appropriate metals and used as contrast agents in x-ray imaging, radionuclide imaging and ultrasound imaging.

Use in Imaging

To use the ligands of this invention for imaging, they must first be complexed with the appropriate metal. This can be accomplished by methodology known in the art. For example, the metal can be added to water in the form of an oxide or in the form of a halide or acetate and treated with an equimolar amount of a ligand of the present invention. The ligand can be added as an aqueous solution or suspension. Dilute acid or base can be added (if needed) to maintain a neutral pH. Heating at temperatures as high as 100° C. for periods up to four hours is sometimes required, depending on the metal and the chelator, and their concentrations.

Pharmaceutically acceptable salts of the metal complexes of the ligands of this invention are also useful as imaging agents. They can be prepared by using a base (e.g., an alkali metal hydroxide, meglumine or arginine) to neutralize the above-prepared metal complexes while they are still in solution. Some of the metal complexes are formally uncharged and do not need cations as counterions. Such neutral complexes are preferred as intravenously administered x-ray and NMR imaging agents over charged complexes because they provide solutions of greater physiologic tolerance due to their lower osmolality.

Sterile aqueous solutions of the chelate complexes can be administered to mammals (e.g., humans) orally, intrathecally and especially intravenously in concentrations of 0.003 to 1.0 molar. For example, for the visualization of brain lesions in canines using magnetic resonance imaging, a gadolinium complex of a ligand of formula I can be administered intravenously at a dose of 0.05 to 0.5 millimoles of the complex per kilogram of animal body weight, preferably at a dose of 0.1 to 0.3 millimoles/kilogram. For visualization of the kidneys, the dose is preferably 0.05 to 0.25 millimoles/kilogram. For visualization of the heart, the dose is preferably 0.25 to 1.0 millimoles/kilogram. The pH of the formulation will be between about 6.0 and 8.0, preferably between about 6.5 and 7.5. Physiologically acceptable buffers (e.g., tris-(hydroxymethyl)aminomethane) and other physiologically acceptable additives (e.g., stabilizers such as parabens) can be present.

It is also advantageous to employ dual scavenging excipients such as those described in a copending application U.S. Ser. No. 682,487 filed Apr. 9, 1991 entitled "DUAL FUNCTIONING EXCIPIENT FOR METAL CHELATE CONTRAST AGENTS". Those excipients have the general formula

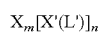

wherein X and X' are independently Ca or Zn, L' is an organic ligand which may be different than or the same as the ligand employed to complex the metal and m and n are independently 1, 2 or 3.

Use of Radiotherapy or Imaging where the Metal-Chelate-Complex is Bound to a Biomolecule The bifunctional metal-chelating ligands can bind to a monoclonal antibody or a fragment thereof for use in radiotherapy. Monoclonal antibodies are useful in that they can be used to target radio-nuclides to cancer or tumor sites with great specificity. The compounds of this invention wherein $R_1$ is other than hydrogen are then linked to monoclonal antibodies or fragments thereof.

The methods of linking the bifunctional chelate to the antibody or antibody fragment are known in the art (Brechbiel, same reference as referred to hereinabove) and will depend primarily on the particular bifunctional chelate and secondarily on the antibody or fragment thereof. For example, when the formula Ia compound is $R_1$=H, $R_2$=—NCS or

one reacts 10 µL of a 5.0 mM aqueous solution of the formula I chelator with 0.5 mL of a 5.0 mg/mL monoclonal antibody (B72.3 purchaseable from Damon Biotech Corporation) in 50 mM Hepes buffer at pH 8.5. 16 µL of 1.5M aqueous triethylamine is added. After 2 hours reaction time, the monoclonal antibody is purified by dialysis. This procedure provides between 1 and 2 formula I chelator molecules bound to each monoclonal antibody. Radioactive metal ion (for example $^{90}Y$) can then be added to the monoclonal antibody-bound chelator by methods known in the art. For example, $^{90}Y$ as the $^{90}Y(III)$ (acetate)$_3$(H$_2$O)$_4$ (approximate formula in aqueous solution) can be reacted with the monoclonal antibody-bound chelate in solutions where the concentration of each is between $10^{-5}$ and $10^{-7}$ and the pH is 6. Dialysis against citrate is then used to purify the product.

An alternative, and preferred method follows that described above, but substitutes the metal-chelate complex for the chelating ligand. To use this method the metal chelate complex is first made by reacting metal-oxide, -halide, -nitrate, -acetate, or the like with formula I chelator. For the chelator described above the acetate of $^{90}Y$ at $<10^{-6}M$ is reacted with the chelator at about $10^{-3}$ at pH 6, the chelate complex is purified by ion exchange or reverse phase HPLC choromatography, and then reacted with the monoclonal antibody described above for the chelator. The bifunctional, metal-containing, linked antibody is used in the following manner. A human or animal with a tumor to which the monoclonal antibody is specific is injected intravenously, subcutaneously, intraperitoneally or intralymphatically for example, with an aqueous solution of the $^{90}Y$-formula I chelator-monoclonal antibody compound. This allows the radioactive metal ion to be directed to the tumor for which it is intended. The intravenous dosage used is 0.1 to 0.4 millicuries per kilogram of body weight.

Preferred embodiments for when the compounds are linked to a protein are when $R_1$ and/or $R_2$=NCS is reacted with protein to produce the protein conjugate. Preferred proteins are those in serum, wherein the $R_1$ and/or $R_2$=NCS compound is directly injected.

It is understood that other functional groups known in the art can be used to link the bifunctional metal-chelating ligands of this invention to monoclonal antibodies or fragments thereof.

$R_1$ and $R_2$ are each

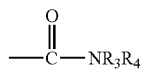

and $R_3$ in each is hydroxyalkyl in a preferred embodiment for forming a Gd(III) chelate useful in general purpose magnetic resonance imaging. The most preferred embodiments for forming a Gd(III) chelate are when the $R_3$ groups are each

—CH$_2$—CH—CH$_2$OH
        |
        OH or —CH(CH$_2$OH)$_2$, especially

—CH$_2$—CH—CH$_2$OH,
        |
        OH and the $R_4$ groups are each hydrogen.

The present invention also includes multimeric forms of the compounds of formula I, such as dimers, trimers, tetramers, etc. Known functional groups and technology as those discussed above regarding conjugation with biomolecules are readily useable to provide such multimers. The functional groups provided onto the phenyl ring

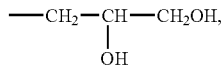

can be, for example, $R_2$=NCS or

especially where $R_{12}$ is methyl or ethyl. Thus, exemplary multimers of formula I

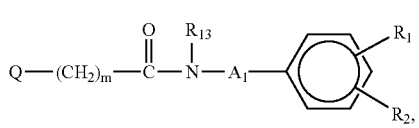

where Q is the aminocarboxylate nucleus of Ia, Ib, Ic or Id, are shown by

Dimers

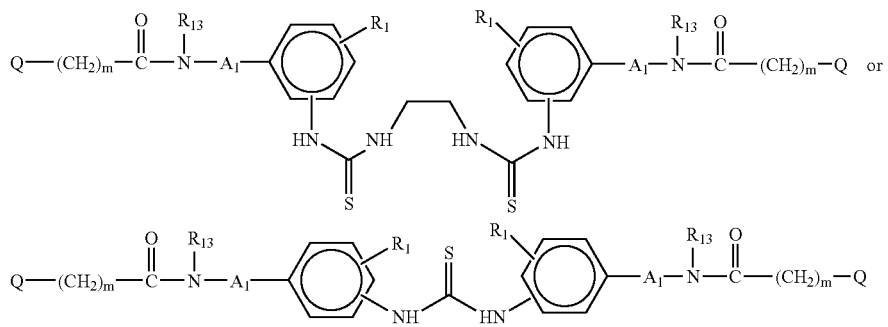

Trimers

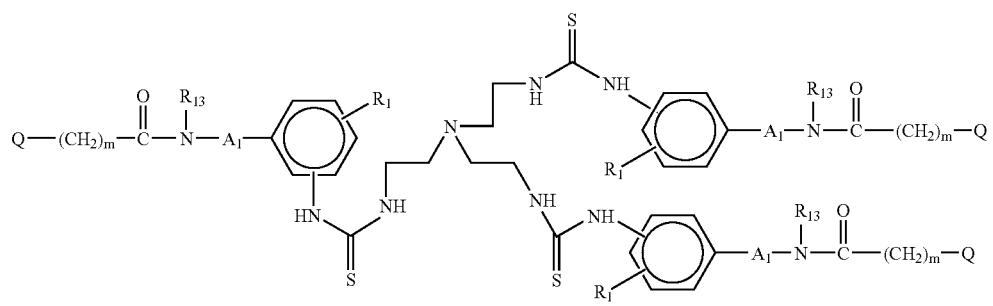

Hexamers

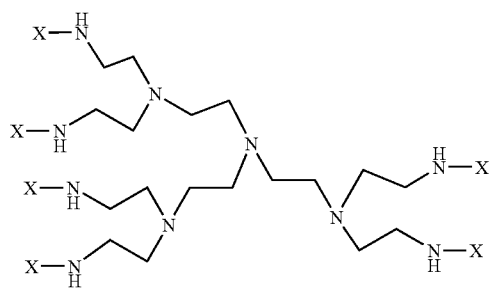

and the like,

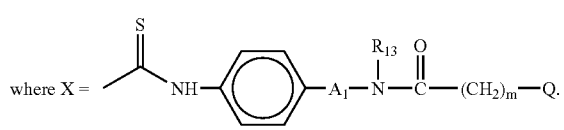

Preparation of Formulae Ia, Ib, Ic and Id Compounds

To prepare the compounds of formula Ia, a compound of the formula

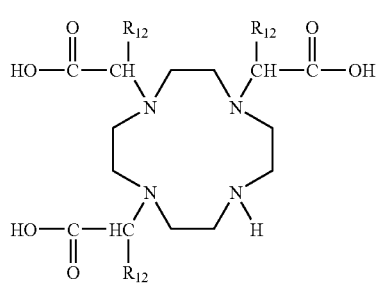

is reacted in a solvent, e.g., water, and in the presence of a base, e.g., sodium hydroxide, with a compound of the formula

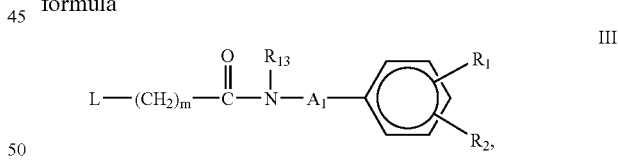

wherein L is a leaving group, such as halogen. The preparation of compounds of formula II is well known, for example, in U.S. Pat. No. 4,885,363 to Tweedle et al. For example, in preparing compounds of formula II, reaction of a compound of the formula

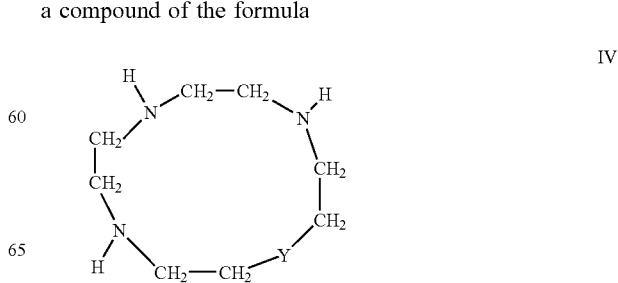

where Y is

with a compound of the formula

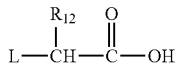

wherein L is a leaving group such as halogen is preferably carried out in water at a pH of about 8.5 to 11 and the temperature of the reaction is maintained at about 45°-55° C. Preferably, only about two equivalents of a compound of formula v are initially used in the reaction; an additional equivalent of the compound of formula V is added in portions starting about 2 to 3 hours after the reaction begins. Total reaction time will preferably be about 8 to 24 hours. The desired trisubstituted product can be separated from the reaction mixture, which includes the mono-, di-, tri- and tetra-substituted derivatives, by techniques recognized in the art including selective precipitation, chromatography and crystallization.

A preferred preparation of the compounds of formula IIa wherein $R_{12}$ is hydrogen is to react 1,4,7,10-tetraazacyclododecane, known in the art, with dimethylformamidedimethylacetal in the presence of benzene to yield 1,4,7,10-tetraazatricyclo-[5.5,1.0]tridecane. This "tricyclic" compound is reacted with an ethanol/water mixture to yield 1-formyl-1,4,7,10-tetraazacyclododecane. This formyl compound is then reacted with t-butyl bromoacetate to yield 1-formyl-4,7,10-triscarboxymethyl-1,4,7,10-tetraazacyclododecane, tris-t-butylester. Finally, the ester groups are removed in the presence of strong acid, such as sulfuric acid, to yield a compound of formula IIa wherein $R_{12}$ is hydrogen. The most preferred methods are included in Dischino, et al., *Inorg. Chem.*, 30, 1265, 1991.

Compounds of formula III wherein $R_1$ and $R_2$ are each

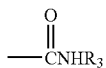

and $R_{13}$ is hydrogen are prepared by first reacting a compound of the formula

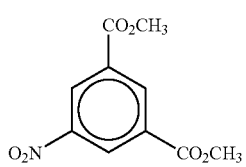

in a solvent, e.g., methanol, with a compound of the formula

to provide the intermediate

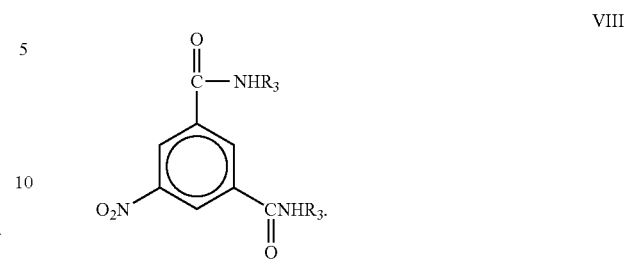

Compounds of formula VIII can thereafter be reduced, e.g., with hydrogen in the presence of a palladium on carbon catalyst, to provide

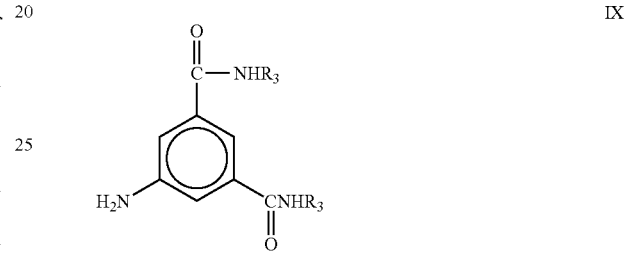

Reaction of compound IX with a compound of the formula

wherein L and L' are the same or different leaving groups, e.g., halogens, in a solvent, e.g., dimethylacetamide, provides the compounds of the formula

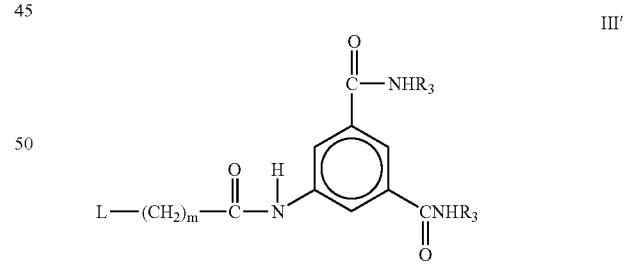

that is, compounds of formula III where $R_1$ and $R_2$ are each

$A_1$ is a single bond, and $R_{13}$ is hydrogen.

In the event that the $R_3$ group in intermediate VIII contains hydroxyalkyl moieties, the hydroxy groups are converted to acetyloxy groups after the reaction of compounds VI and VII to obtain VIII'. For example, if the compound of formula VII is

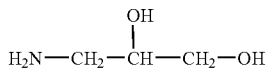

VII' reaction as described above with compound VI provides

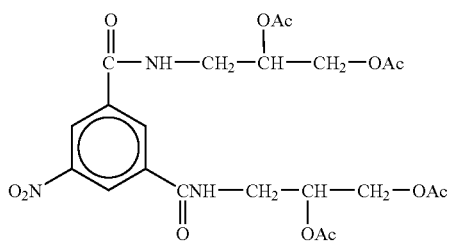

VIII' wherein Ac is acetyl. Following reduction to the corresponding aniline and thereafter reaction with compound X, the corresponding intermediates of III' i.e., wherein $R_3$ is acetyloxy alkyl, are converted to their hydroxyalkyl counterparts by known treatment, e.g., with sodium methoxide in a solvent, for example, methanol.

Compounds of formula III wherein $A_1$ is —$CH_2$—, $R_{13}$ is as defined above, L is chloro and $R_1$ and $R_2$ are each

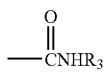

are prepared by first reacting a compound of the formula

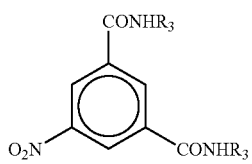

VIII with gaseous hydrogen in the presence of a catalyst such as palladium on carbon in dilute mineral acid to provide the aniline

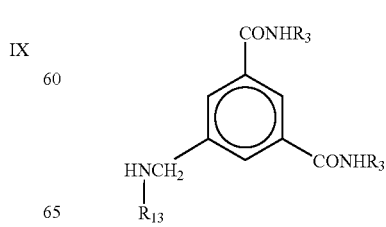

IX

The aniline is diazotized with nitrous acid in acidic medium and then treated with sodium cyanide to obtain

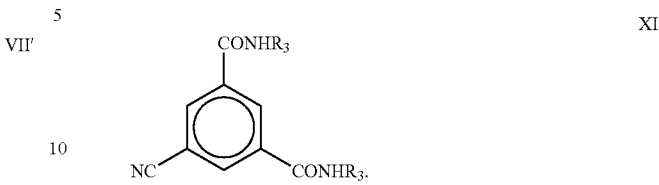

XI

Reduction of the nitrile XI in the presence of a platinum catalyst with gaseous hydrogen at low pressure, for example 3 atmospheres, affords

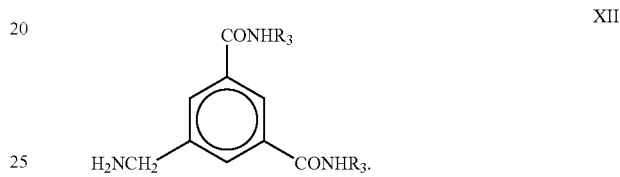

XII

Reaction of XII with a compound of formula

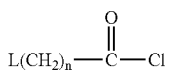

XIII wherein L is a leaving group, for example chlorine, provides compounds of the formula

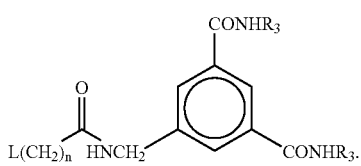

III''

If $R_{13}$ is other than hydrogen, for example methyl, the compound of the formula XII is treated with an aldehyde $R_8CHO$, for example formaldehyde, wherein $R_8$ is H, under reducing conditions, for example with sodium borohydride, to obtain

IX' wherein $R_{13}$ is methyl. Reaction of IX' with the chloride of formula XIII will provide the desired intermediate of the formula

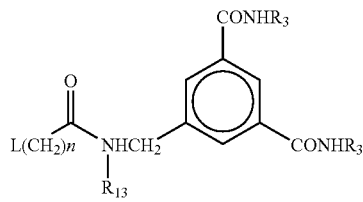

Similarly, compounds of formulae Ib, Ic and Id can be prepared by reacting the various compounds of formula III in a solvent, e.g. water, and in the presence of a base, e.g., sodium hydroxide with the corresponding compounds

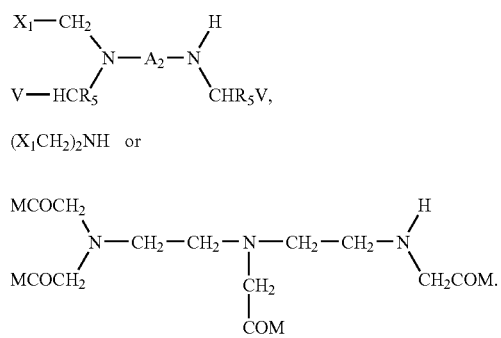

Compounds of formula IIb and IIc are described in U.S. Pat. No. 4,647,447. Compounds of formula IId are described in U.S. Pat. No. 4,859,451.

The invention will now be further described by the following examples, but is not limited to the details therein.

EXAMPLE 1

10-[2-[[3,5-Bis[[(2,3-dihydroxypropyl)amino]-carbonyl]phenyl]amino]-2-oxoethyl]-1,4,7,10-tetraazacyclododecane-1,4,7-triacetic acid, monogadolinium complex A. N,N'-Bis[2,3-bis(acetyloxy)propyl]-5-nitro-1,3-benzenedicarboxamide To a solution of dimethyl-5-nitroisophthalate (23.9 g, 100 mmol) in methanol (300 mL) was added 1-amino-2,3-propanediol (20.2 g) and the mixture was refluxed for 48 hours. Methanol was removed in vacuo, the residue was dissolved in pyridine (150 mL) and then treated with acetic anhydride (80 mL) at room temperature for 16 hours. Excess acetic anhydride was decomposed by adding water (50 mL) to the reaction mixture. The solvents were removed in vacuo, the residue dissolved in ethyl acetate (400 mL) and washed with water (2×100 mL), 10% hydrochloric acid (200 mL) and finally with brine (100 mL). The ethyl acetate layer was dried and removal of the solvent afforded the title A nitro-bis-amide (51.8 g), as a light yellow viscous syrupy material. This was used directly without further purification in the next step.

B. 5-Amino-N,N'-bis[2,3-bis(acetyloxy)propyl]-1,3-benzenedicarboxamide

A solution of the title A nitrobisamide (31.5 g, 60 mmol) in methanol (180 mL) was hydrogenated over 10% palladium on carbon (300 mg) for a period of 3 hours. The catalyst was filtered off and the solvent removed in vacuo to afford pure title B aniline (28.6 g), as a viscous syrupy material. This was used directly without further purification in the next step.

C. N,N'-Bis[2,3-bis(acetyloxy)propyl]-5-N-[(chloroacetyl)amino]-1,3-benzenedicarboxamide The title B aniline was dissolved in dimethylacetamide (150 mL) and treated with chloroacetyl chloride (11.28 g, 100 mmol) dropwise over a period of 20 minutes. The solution was stirred for 3 hours and dimethylacetamide removed in vacuo. The residue that resulted was dissolved in ethyl acetate, washed with water, 10% aqueous sodium bicarbonate, and finally with water. The ethyl acetate layer was dried and removal of the solvent afforded the crude chloroacetanilide (32.0 g). The crude material was purified by column chromatography over silica gel to obtain the title C compound (26.3 g), as a colorless glassy solid. An analytical sample was prepared by crystallizing 1.00 g of the glassy solid from ethyl acetate/hexane. m.p. _____ (68°-72°)

Elemental Analysis calc'd for $C_{24}H_{30}N_3ClO_{11}$: C, 50.40; H, 5.29; N, 7.35; Cl, 6.20; O, 30.77%. Found: C, 50.28; H, 5.15; N, 7.11; Cl, 6.25%.

D. 5-[(Chloroacetyl)amino-N,N'-bis[2,3-dihydroxypropyl]-1,3-benzenedicarboxamide A solution of the title C compound (25.6 g, 45 mmol) in methanol (200 mL) was treated with sodium methoxide (20 mmol) and the solution was stirred at 0° for 30 minutes. The pH of the reaction mixture was adjusted to 7 by adding Dowex 50 ($H^+$) resin, the resin filtered off and the methanol removed in vacuo to afford pure title D compound as a colorless glassy solid (16.8 g). This material was directly used in the next step without further purification.

E. 10-[2-[[3,5-Bis[[(2,3-dihydroxypropyl)amino]-carbonyl]phenyl]amino]2-oxoethyl]1,4,7,10-tetraazacyclododecane-1,4,7-triacetic acid A solution of DO3A sulfate (DO3A=1,4,7,-triscarboxymethyl-1,4,7,10-tetraazacyclododecane prepared in U.S. Pat. No. 4,885,363 to Tweedle et al.) (12.0 g, 27 mmol) was made in water (80 mL) and the pH of the solution was adjusted to 9.8 by adding 5 M sodium hydroxide. While maintaining the pH of the solution at 9.8, a solution of the title D compound (16.4 g, 40.6 mmol) in water (50 mL) was slowly added to the DO3A solution at 80° over a period of 45 minutes. At the end of 17 hours, the reaction mixture was cooled to room temperature, the pH lowered to 3.5 by adding 1 N hydrochloric acid and the solution was desalted by cation exchange chromatography. Further purification by anion exchange chromatography afforded the title E compound as the triethylammonium salt (19.9 g). The triethylamine salt was dissolved (6.00 g) in water (1 L), applied to an anion exchange column and then eluted with 50 mM formic acid to obtain the desired title E compound (4.9 g). IR: 3400 (OH); 3115 (NH); 1631 (COOH and ArCONH) $cm^{-1}$. Mass Spectrum: 714 $(M+H)^+$; 712 $(M-H)^-$.

Elemental Analysis calc'd for $C_{30}H_{47}N_7O_{13} \cdot 0.38H_2O$: C, 50.01; H, 6.68; N, 13.61; O, 29.71%. Found: C, 49.91; H, 6.97; N, 13.42; $H_2O$, 0.95.%.

F. 10-[2-[[3,5-Bis[[(2,3-dihydroxypropyl)amino]-carbonyl]phenyl]amino]-2-oxoethyl]-1,4,7,10-tetraazacyclododecane-1,4,7-triacetic acid, monogadolinium salt To a solution of the title E triethylammonium salt (19.00 g, 18.7 mmol) in water (80 mL) at pH 4.72 was added a solution of $Gd(OAc)_3 \cdot 4H_2O$ (9.83 g, 24 mmol) in water (80 mL) and the reaction mixture was stirred at room temperature for 12 hours. The reaction mixture was subjected to low pressure reversed phase column chromatography over a styrene-divinylbenzene copolymer resin to obtain the title compound as a colorless glassy solid (17.5 g). The pure product (17.00 g) was crystallized from hot methanol to afford this title F compound as colorless needles of >99.9% purity. This sample was redissolved in water (200 mL), the solvent removed, and the sample dried in vacuo (1 mm) for four days at 80°. Mass Spectrum: 869 $(M+H)^+$, 867 $(M-H)^{-1}$.

Elemental Analysis: calc'd for $C_{30}H_{44}N_7O_{13} \cdot 0.36\ H_2O$: C, 41.20; H, 5.15; N, 11.21; O, 24.45%. Found: C, 40.96; H, 5.07; N, 10.93; $H_2O$, 0.75.%.

EXAMPLE 2

10-[2-[[3,5-Bis-[[[2-hydroxy-1-(hydroxymethyl)ethyl]-amino]carbonyl]phenylamino]2-oxoethyl]1,4,7,10-tetraazacyclododecane-1,4,7-triacetic acid

A. N,N'-bis[2-(Acetyloxy)-1-[(acetyloxy)methyl]-ethyl]-5-nitro-1,3-benzenedicarboxamide To a solution of dimethyl-5-nitroisophthalate (14.0 g, 58 mmol) in methanol (150 mL) was added 2-amino-1,3-propanediol (16.5 g, 181 mmol) and the mixture was refluxed for 48 hours. The reaction mixture was cooled to room temperature and the crystalline solid that separated out filtered and dried to obtain the bis amide (19.5 g). A solution of the bis-amide (19.0 g) in pyridine (75 mL) was treated with acetic anhydride (40 mL) at room temperature for 16 hours. Excess acetic anhydride was decomposed by adding water (50 mL) to the reaction mixture. The solvents were removed in vacuo, the residue dissolved in ethyl acetate, and the solution washed with water, 10% hydrochloric acid and finally with brine. The ethyl acetate layer was dried and removal of the solvent afforded pure title A nitrobisamide (23.6 g) as a colorless solid, after crystallization from acetone and hexane, m.p. 105-107° C.

B. 5-Amino-N,N'-bis[2-(acetyloxy)-1-[(acetyloxy)-methyl]ethyl]-1,3-benzenedicarboxamide A solution of the title A compound (18.0 g, 34 mmol) in methanol (180 mL) was hydrogenated over palladium on carbon (0.5 g) for a period of 3 hours. The catalyst was filtered off and the solvent removed in vacuo to afford pure title B aniline (16.6 g) after crystallization from acetone and hexane, m.p. 152-154° C.

Elemental Analysis calc'd for $C_{24}H_{30}N_3ClO_{11}$: C, 50.40; H, 5.29; N, 7.35; Cl, 6.20%. Found: C, 50.64; H, 5.20; N, 7.22; Cl, 6.57.%.

C. N,N'-Bis[2-(acetyloxy)-1-[(acetyloxy)methyl]-ethyl]-5-(chloroacetyl)amino-1,3-benzenedicarboxamide The title B compound (17.0 g, 34 mmol) was dissolved in dimethylacetamide (150 mL) and treated with chloroacetyl chloride (7.52 g, 64 mmol) dropwise over a period of 20 minutes. The solution was stirred for 3 hours and dimethylacetamide was then removed in vacuo. The residue that resulted was dissolved in ethyl acetate, washed with water, saturated aqueous sodium bicarbonate solution, and finally with water. The ethyl acetate layer was dried and the solvent removed to obtain the crude chloroacetanilide (18.5 g). This material was crystallized from ethyl acetate and hexane to afford pure title C compound (16.8 g), m.p. 135-137° C.

Elemental Analysis calc'd for $C_{24}H_{30}N_3ClO_{11}$: C, 50.40; H, 5.29; N, 7.35; Cl, 6.20; O, 30.77%. Found: C, 50.64; H, 5.20; N, 7.22; Cl, 6.57%.

D. 5-[(Chloroacetyl)amino]-N,N'-bis[2-hydroxy-1-(hydroxymethyl)ethyl]-1,3-benzenedicarboxamide A solution of the title C compound (16.0 g, 28 mmol) in methanol (200 mL) was treated with sodium methoxide (10 mmol) and the solution stirred at 0° for 30 minutes. The precipitated solid was filtered and dried to afford pure title D compound as a colorless glassy solid (10.8 g), m.p. 222-224°. Mass Spectrum: m/z 404 $(M+H)^+$.

Elemental analysis calc'd for $C_{16}H_{22}N_3ClO_7$: C, 47.59; H, 5.49; N, 10.41; Cl, 8.78; O, 27.73%. Found: C, 47.66; H, 5.55; N, 9.98; Cl, 8.88%.

E. 10-[2-[[3,5-Bis-[[[2-hydroxy-1-(hydroxy-methyl)ethyl]amino]carbonyl]phenylamino]2-oxoethyl]-1,4,7,10-tetraazacyclododecane-1,4,7-triacetic acid A solution of DO3A sulfate (6.0 g, 13.5 mmol) was made in water and the pH of the solution was adjusted to 9.8 by adding 5 M sodium hydroxide. While maintaining the pH of the solution at 9.8, solid N,N'-bis[2-hydroxy-1-[(hydroxy)methyl]ethyl]-5-N-(chloroacetyl)aminobenzene-1,3-dicarboxamide (8.2 g, 20.4 mmol) was added in small portions to the DO3A solution at 80° over a period of 45 minutes. At the end of 20 hours, the reaction mixture was cooled to room temperature, the pH lowered to 3.5 by adding 1 N hydrochloric acid and the solution was desalted by cation exchange column chromatography. Further purification by anion exchange column chromatography afforded the title E compound as the corresponding triethylammonium salt (5.2 g). The triethylammonium salt (5.2 g) was dissolved in water (1 L) and applied to an anion exchange column and eluted with 50 mM formic acid to obtain the pure title E compound (4.4 g), as a colorless glassy solid.

Elemental analysis calc'd for $C_{30}H_{47}N_7O_{13}$: C, 50.48; H, 6.64; N, 13.74; O, 29.14%. Found: C, 50.34; H, 6.83; N, 13.54%.

F. The Gadolinium Chelate of Title E Compound

The Gd complex of this ligand was prepared by the same method used for the compound in Example 1.

Elemental Analysis for $C_{30}H_{44}N_7O_{13}Gd\ 3.48\ H_2O$: C, 38.72; H, 5.52; N, 10.53; O, 28.33%. Found: C, 39.01; H, 5.37; N, 10.26%.

EXAMPLE 3

10-[2-[[3,5-Bis[[(2-methylbutyl)amino]carbonyl]-phenyl]amino]2-oxoethyl]1,4,7,10-tetraazacyclododecane-1,4,7-triacetic acid, monogadolinium complex

A. N,N'-Bis[(2-methylbutyl)amino]-5-nitro-1,3-benzenedicarboxamide

To a solution of dimethyl-5-nitro-isophthalate (14.0 g, 50 mmol) in methanol was added 2-methylbutylamine (12.5 g, 150 mmol) and the mixture was refluxed for 48 hours. Methanol was removed in vacuo, the residue dissolved in ethyl acetate and washed with 10% hydrochloric acid, 10% aqueous sodium bicarbonte solution and finally with water. The ethyl acetate layer was dried and removal of the solvent afforded the desired compound. This was crystallized from ethyl acetate and hexane to afford the the title A compound as colorless needles (19.6 g), m.p. 147-148° C.

Elemental Analysis for C, 61.87; H, 7.79; N, 12.03; O, 18.31%. Found: C, 61.84, H, 7.76; N, 12.02%.

B. 5-Amino-N,N'-bis[(2-methylbutyl)amino]-1,3-benzenedicarboxamide

A solution of the title A compound (17.45 g, 50 mmol) in methanol (180 mL) was hydrogenated over 10% palladium on carbon (500 mg) for a period of 3 hours. The catalyst was filtered off and the solvent removed in vacuo to afford the title aniline as a colorless solid. This was crystallized from acetone and hexane to afford the title B compound as colorless needles (15.8 g), m.p. 170-172° C.

Elemental Analysis for C, 67.87; H, 9:15; N, 13.15; O, 12.02%. Found: C, 68.07, H, 9.30; N, 13.26%.

C. 5-[(Chloroacetyl)amino]-N,N-bis[(2-methyl-butyl)amino]1,3-benzenedicarboxamide A solution of the title B compound (11.48 g, 36 mmol) in dimethylacetamide (200 mL) was treated with chloroacetyl chloride (5.6 g, 50 mmol) dropwise over a period of 20 minutes. The solution was stirred for 3 hours and dimethylacetamide removed in vacuo. The residue that resulted was dissolved in ethyl acetate (200 mL), washed with water (100 mL), 10% aqueous sodium bicarboante (100 mL) and finally with water (100 mL). The ethyl acetate layer was dried and removal of the solvent afforded the crude chloroacetanilide (12.8 g). This was crystallized from ethyl acetate and hexane to afford the title C compound as colorless needles (11.2 g), m.p. 160-162° C.

Elemental Analysis for C, 60.67; H, 7.64; N, 10.61; Cl, 8.95; O, 12.12%. Found: C, 61.03, H, 7.69; N, 10.57; Cl, 9.22%.

D. 10-[2-[[3,5-Bis[[(2-methylbutyl)amino)-carbonyl]phenyl]amino]2-oxoethyl]1,4,7,10-tetraazacyclododecane-1,4,7-triacetic acid A solution of DO3A sulfate (6.0 g, 13.5 mmol) was made in water (100 mL) and the pH of the solution was adjusted to 9.8 by adding 5 M sodium hydroxide. While maintaining the pH of the solution at 9.8, a solution of the chloroacetanilide (8.2 g, 27 mmol) in ethanol (100 mL) was slowly added to the DO3A solution at 80° over a period of 1 hour. At the end of 17 hours, the reaction mixture was cooled to room temperature, the pH lowered to 3.5 by adding 1N hydrochloric acid and the solution was desalted by cation exchange chromatography. Further purification by anion exchange chromatography afforded the title compound as the triethyl ammonium salt (2.8 g). The triethyl ammonium salt was dissolved in water, applied to an anion exchange column and then eluted with 50 mM formic acid to obtain the desired compound (AAA-DO3A) (2.2 g). A small amount of an impurity present in this sample was further removed by a reverse phase CHP-20 column chromatography to afford the title compound as a colorless glassy solid (1.8 g). Mass Spectrum: 706 (M+H)$^+$; 704 (M−H)$^-$.

Elemental analysis calc'd for $C_{34}H_{55}N_7O_9 \cdot 1.7\ H_2O$: C, 55.45; H, 7.99; N, 13.31; O, 23.24. Found: C, 55.85; H, 8.37; N, 13.19; $H_2O$: 4.15.

E. Gadolinium Chelate of Title D Compound

The Gd complex of this ligand was prepared by the same method as used for the compound of Example 1.

Elemental anal. calc'd for $C_{34}H_{52}N_7O_9Gd, 6.44\ H_2O$: C, 41.84; H, 6.70; N, 10.04; O, 26.31%. Found: C, 41.80; H, 6.65; N, 10.28%.

The $T_1$ relaxivity was measured for nine prior art gadolinium complexes (1-9) as compared to novel gadolinium complexes using the ligands of Examples 1, 2 and 3 (#10, 11 and 12, respectively, in the Table below). Relaxivity was measured on an IBM Minispec spin analyzer operating at 20 MHz and 39±1° C. Aqueous solutions were used in 0.1-5 mM Gd concentration range.

---

Structures of Ligands for Gd Complexes of Table 1

1. DTPA

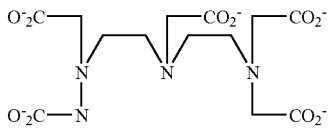

2. DTPA-HA

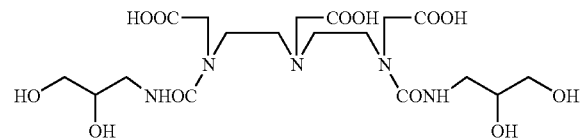

3-12.

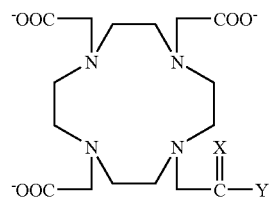

| | | |
|---|---|---|
| 3. | DOTA | Y = O<br>Y = O$^-$ |
| 4. | NH$_2$-DO3A | X = O<br>Y = —NH$_2$ |
| 5. | MA-DO3A | X = O<br>Y = —NHCH$_3$ |
| 6. | HEA-DO3A | X = O<br>Y = —NHCH$_2$CH$_2$OH |
| 7. | PA-DO3A | X = O<br>Y = —NHPhenyl |

Structures of Ligands for Gd Complexes of Table 1

| | | |
|---|---|---|
| 8. | HP-DO3A | X = OH, H<br>Y = —CH₃ |
| 9. | PG-DO3A | X = OH, H<br>Y = 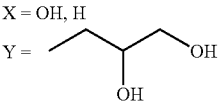 |
| 10. | HAA-DO3A (Ex. 1) | X = O<br>Y = -NH— 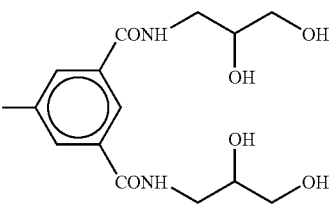 |
| 11. | HAS-DO3A (Ex. 2) | X = O<br>Y = -NH— 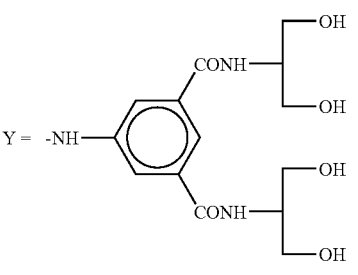 |
| 12. | AAA-DO3A (Ex. 3) | X = O<br>Y = -NH— 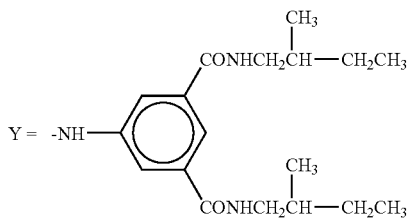 |

TABLE 1

Data on Water Soluble Gd Complexes and Ions Demonstrating The Enhancement of Relaxivity by N-Hydroxy-alkyl or N-alkyl-isophthalamide Groups and by Aryl Groups or by Hydroxyalkyl or Alkylamido Groups.

| Gd(L), L = | $T_1$ Relaxivity |
|---|---|
| 1. DTPA | 3.7 |
| 2. DTPA-HA | 4.4 |
| 3. DOTA | 3.4 |
| 4. NH₂-DO3A | 3.6 |
| 5. MA-DO3A | 4.3 |
| 6. HEA-DO3A | 4.3 |
| 7. PA-DO3A | 4.1 |
| 8. HP-DO3A | 3.7 |
| 9. PG-DO3A | 3.4 |
| 10. HAA-DO3A (Ex. 1) | 5.8 |
| 11. HAS-DO3A (Ex. 2) | 5.4 |
| 12. AAA-DO3A (Ex. 3) | 5.9 |

The relaxivity is especially high only in the substituted aryl compounds, 10, 11 and 12, i.e., Gd(HAA-DO3A), Gd(HAS-DO3A) and Gd(AAA-DO3A). One or two hydroxy groups alone do not enhance relaxivity, as can be seen from L=HP-DO3A, PG-DO3A. Alkyl or aryl substituents only slightly enhance relaxivity, as seen from MA-DO3A and PA-DO3A. Both alkyl and hydroxyalkyl substituents on the aromatic are effective at enhancing relaxivity (the hydroxyalkyls are preferred for their increased water solubility).

EXAMPLE 4

10-[2-[Methyl[3,5-bis[[(2-methylbutyl)amino]-carbonyl]phenyl]amino]-2-oxoethyl]-1,4,7,10-tetraaza-cyclododecane-1,4,7-triacetic acid, monogadolinium salt

A. N,N'-bis(2-Methylbutyl)-5-[[(phenylmethoxy)-carbonyl]-amino]-1,3-benzenedicarboxamide To a cooled solution of compound A from Example 3 (15.4 g, 46 mmol) in anhydrous DMA (75 ml) at 0° C. was added benzyl chloroformate (9.4 g, 55.2 mmol). The clear solution was stirred at 0° C. for 2 hours. DMA was removed in vacuo. The residue was dissolved in EtOAc (150 ml), and was washed with aqueous NaHCO₃ solution (30 ml) and with H₂O (2×50 ml). The organic layer was dried over anhydrous MgSO₄ and the solvent removed to obtain the crude product as an oily liquid. Recrystallization of the crude material from EtOAc/hexanes afforded the title A product as a white solid (17.0 g), m.p. 130.5-132.5° C.

Elemental analysis calc'd for $C_{26}H_{35}N_3O_4$: C, 68.85; H, 7.78; N, 9.26; O, 14.11%. Found: C, 68.64; H, 7.91; N, 9.20%.

B. N,N'-bis(2-Methylbutyl)-5-[methyl[(phenylmethoxy)carbonyl]amino]-1,3-benzenedicarboxamide To a suspension of NaH (0.58 g, 24.2 mmol) in anhydrous THF (25 ml) was added a solution of the title A compound (10.0 g, 22 mmol) in anhydrous THF (60 ml). MeI (15.7 g, 110 mmol) was added and the reaction mixture was stirred at room temperature for 1 hour. THF was removed in vacuo. The solid was dissolved in EtOAc and washed with H₂O and then with aqueous NaCl solution. The EtOAc layer was dried over anhydrous MgSO₄ and the solvent removed to obtain the title B compound.

Elemental analysis calc'd for $C_{27}H_{37}N_3O_4$: C, 69.35; H, 7.98; N, 8.99; O, 13.69%. Found: C, 69.10; H, 8.03; N, 8.91%.

C. 5-(Methylamino)-N,N'-bis(2-methylbutyl)-1,3-benzenedicarboxamide

To a solution of the title B compound (13 g, 27.8 mmol) in MeOH (50 ml) was added 1,4-cyclohexadiene (20 ml) and 10% Pd/C (3.25 g). The mixture was refluxed for 0.5 hour. The solid was filtered through a celite cake and the solvent was removed to obtain the crude product. Recrystallization from hot EtOAc afforded the title C product as white crystals (5.2 g), m.p. 160.1-160.8° C.

Elemental analysis calc'd for $C_{19}H_{31}N_3O_2$: C, 68.43; H, 9.37; N, 12.60; O, 19:60%. Found: C, 68.13; H, 9.50; N, 12.57%.

D. 5-[(Chloroacetyl)methylamino]-N,N'-bis(2-methylbutyl)-1,3-benzenedicarboxamide To a solution of the title C compound (5.2 g, 15.6 mmol) in anhydrous DMA (150 ml) was added chloroacetyl chloride (2.43 g, 5.9 mmol). The solution was stirred at room temperature for 1.5 hours. The mixture was cooled. Water (20 ml) was added and the solvent removed in vacuo. The residue was dissolved in EtOAc and washed with aqueous $NaHCO_3$ solution, then with water. The organic layer was dried over anhydrous $MgSO_4$ and the solvent removed to obtain the crude product. Recrystallization from hot EtOAc afforded the title D compound as white crystals (6.0 g), m.p. 170.0-171.5° C.

Elemental analysis calc'd for $C_{21}H_{32}N_3O_3Cl$: C, 61.53; H, 7.87; N, 10.25; Cl, 8.65; O, 11.71%. Found: C, 61.77; H, 7.83; N, 10.39; Cl, 8.41%.

E. 10-[2-Methyl[3,5-bis[[(2-methylbutyl)amino]-carbonyl]phenyl]amino]-2-oxoethyl]-1,4,7-10-tetraazacyclododecane-1,4,7-triacetic acid DO3A sulfate (4.35 g, 9.8 mmol) was dissolved in $H_2O$ (100 ml) and the pH of the solution adjusted to 9.8 by adding 10 N NaOH. To this solution at 85° C. was added a solution of the title D compound (5.7 g, 13.9 mmol) in EtOH (100 ml) over a period of 45 minutes. The pH was maintained at 9.8 by adding 5 N NaOH. The mixture was heated at 85° C. for 44 hours. The solvents were removed in vacuo. The solid was dissolved in $H_2O$ (300 ml) and EtOAc (100 ml) and the cloudy solution was stirred at 85° C. for 2 hours until the mixture turned clear. The two layers were separated. The aqueous layer (pH 7) which contained the crude product was applied to a 300 ml column of CHP-20 resin using EtOH/$H_2O$ (0-10%) as an eluent. The fractions containing the desired compound were combined and removal of the solvent afforded the title E product as a monosodium salt (2.9 g).

Elemental analysis calc'd for C, 54.86; H, 7.68; N, 13.17; O, 19.76%. Found: C, 54.84; H, 8.09; N, 12.73%.

F. 10-[2-[Methyl[[3,5-bis[[(2-methylbutyl)amino]-carbonyl]phenyl[amino]-2-oxoethyl]-1,4,7,10-tetraazacyclododecane-1,4,7-triacetic acid, monogadolinium salt The title E compound (700 mg, 0.97 mmol) was dissolved in H2O (8 ml) and the pH of the solution adjusted to 4.5 by adding diluted HOAc. To this solution was added a solution of $Gd(OAc)_3.4H_2O$ (1.21 g, 1.3 mmol) in $H_2O$ (10 ml). The mixture was stirred at 45° C. for 24 hours. The solution was then applied to a 600 ml column of CHP-20 resin, using EtOH/$H_2O$ (0-50%) as an eluent. The fractions containing the desired compound were combined and removal of the solvent afforded 770 mg of the title product.

Elemental analysis calc'd for $C_{34}H_{52}N_7O_9Gd.1.10H_2O$: C, 46.42; H, 6.21; N, 11.14; Gd, 18.28; O, 16.74%. Found: C, 46.68; H, 6.35; N, 10.88%.

EXAMPLE 5

10-[2-[[4-[[2,3-Dihydroxypropyl)amino]carbonyl]-phenyl]amino]-2-oxoethyl-1,4,7,10-tetraazacyclododecane-1,4,7-triacetic acid, monogadolinium salt

A. N-(2,3-Diacetylpropyl)-4-carboxyamidonitrobenzene

To a solution of methyl 4-nitro benzoate (18.1 g, 100 mmol) in 200 ml of MeOH was added 3-amino-1,2-propanediol (18.2 g, 200 mmol) and the mixture was refluxed for 24 hours. The product then was directly acetylated. Methanol was removed in vacuo. The residue was dissolved in 100 ml of pyridine and 80 ml of acetic anhydride was added. The solution was stirred at room temperature for 24 hours. The solution was cooled and water was added to decompose the excess acetic anhydride. The solvents were removed in vacuo. The residue was dissolved in EtOAc and it was washed with $H_2O$, 10% HCl and finally with brine. The organic layer was dried and removal of the solvent afforded 28.3 g of the title A compound as a yellowish solid (87.3 mmol), m.p. 101.5-102.8°.

Elemental analysis calc'd for $C_{14}H_{16}N_2O_7$: C, 51.85; H, 4.97; N, 8.64. Found: C, 51.69; H, 5.00; N, 8.58.

B. N-(2,3-Diacetylpropyl)-4-carboxyamido aniline

A solution of the title A compound (12 g, 37 mmol) in 120 ml of EtOAc was mixed with 5% Pd/c (1.2 g). The solution was hydrogenated at 45 psi pressure until the pressure dropped down to a constant value. The solid was then filtered. The filtrate was concentrated to dryness and 10.8 g of the title B product as a foaming liquid was obtained (36.7 mmol). TLC: Silica gel, $R_f$ 0.70, EtOAc, visualized by UV.

C. 4[(Chloroacetyl)amino]-N-(2,3-dihydroxy-propyl)-1-benzenecarboxamide

To a cooled solution of the title B compound (9.3 g, 31.6 mmol) in 120 ml of anhydrous DMA was added chloroactyl chloride (5.3 g, 46.9 mmol). The solution was stirred at room temperature for 1 hour. The mixture was cooled, 20 ml of saturated aqueous $NaHCO_3$ solution added and the mixture was concentrated in vacuo. The residue was dissolved in EtOAc and the organic layer washed with $H_2O$ and brine. The organic layer was dried over anhydrous MgSO4 and evaporated to dryness. To deprotect the acetate groups, the residue was dissolved in 130 ml of MeOH. To this solution, a solution of 230 mg Na in 5 ml MeOH was added. It was stirred at room temperature for 1 hour. Dowex 50 ($H^+$ form) was added until pH 7. The resin was filtered and the solution was concentrated to a volume of 50 mL.

Crystallization of the product gave 6.2 g of solid title C compound (21.6 mmol), m.p. 184.6-185.5° C.

Elemental analysis calc'd for $C_{12}H_{15}N_2O_4Cl$: C, 50.40; H, 5.39; N, 9.48; Cl, 12.00. Found: C, 50.78; H, 5.28; N, 9.59; Cl, 12.19.

D. 10-[2-[[4-[[(2,3-Dihydroxypropyl)amino]-carbonyl]phenyl]amino]-2-oxoethyl]-1,4,7,10-tetraazacyclododecane-1,4,7-triacetic acid DO3A sulfate (6.0 g, 13.5 mmol) was dissolved in 200 ml of $H_2O$ and the pH of the solution was adjusted to 9.8 by adding 10 N NaOH. To this solution at 85° C. was added a solution of the title C compound (5.8 g, 20.2 mmol) in 200 ml of EtOH over a period of 45 minutes. The pH was maintained at 9.8 by adding 5 N NaOH. As the reaction proceeded, the mixture turned clear. The mixture was heated at 85° C. for 26 hours. The solvents were removed in vacuo. The crude material was dissolved in 500 ml of H2O and applied to a 2-liter column of anion exchange resins. The column was eluted with a gradient of $Et_3NH^{+-}HCO3$ buffer, 5 mM to 200 mM. The fractions containing the desired compound were combined and concentrated in vacuo. The title D compound (6.1 g) was obtained as the mono triethylammonium salt (8.8 mmol).

Elemental analysis calc'd for $C_{32}H_{55}N_7O_{10}.0.29H_2O$: C, 54.67; H, 7.97; N, 13.95. Found: C, 54.71; H, 8.14; N, 13.94.

E. 10-[2-[[4-[[(2,3-Dihydroxypropyl)amino]-carbonyl]phenyl]amino]-2-oxoethyl]-1,4,7,10-tetraazacyclododecane-1,4,7-triacetic acid, monogadolinium salt 700 mg (1.0 mmol) of the title D compound (mono triethylammoniun salt) was dissolved in 10 ml of $H_2O$ and the pH of the solution adjusted to 4.5 by adding diluted HOAc. To this solution was added a solution of $Gd(OAc)_3 \cdot 4H_2O$ (540.4 mg, 1.3 mmol) in 15 ml of $H_2O$. The mixture was stirred at 45° C. for 24 hours. The solution was then diluted and applied to a column of CHP-20 resin. The column was eluted with $H_2O$, then with increasing amount of EtOH (5-20%). Evaporation of the combined fractions containing the desired product afforded 300 mg of the pure title compound (0.40 mmol).

Elemental analysis calc'd for $C_{26}H_{37}N_7O_{10}Gd.0.82H_2O$: C, 40.79; H, 5.09; N, 10.98. Found: C, 40.81; H, 5.14; N, 10.91.

EXAMPLE 6

10-[N-(4-Nitrophenyl)acetamido]-1,4,7,10-tetraazacyclododecane-1,4,7-triacetic acid, monogadolinium salt

A. 10-[N-(4-Nitrophenyl)acetamido]-1,4,7,10-tetraazacyclododecane-1,4,7-triacetic acid A solution of 2-chloro-4'-nitroacetanilide (3 g, 14 mmol) in DMSO (30 ml) was slowly added into a solution of DO3A (5.8 g, 16.8 mmol) in water (30 ml) whose pH was adjusted to 10 by the addition of 10 N NaOH at 50° C. The reaction was maintained at 50°-60° C. and the pH was kept at 10 for 54 hours. The yellow precipitate was filtered and dissolved in water (150 ml). The pH of the resulting solution was adjusted to ca.2 by the addition of 1.0 N HCl. The resulting solution was then applied to a column of CHP-20P resin. The column was eluted with water (3 L), followed by 5% (1 L). 10% (1 L) and 20% (1.5 L) EtOH containing water in the order maintained. The fractions containing the desired compound were combined and concentrated in vacuo to give the yellow title A product (2.6 g).

Analysis calc'd for $C_{22}H_{32}N_6O_9$ 1.30 $H_2O$: C, 48.23; H, 6.36; N, 15.34; O, 30.07%. Found: C, 47.94; H, 6.48; N. 15.72; $H_2O$, 4.26%.

B. 10-[N-(4 Nitrophenyl)acetamido]-1,4,7,10-tetraazacyclododecane-1,4,7-triacetic acid, monogadolinium salt The title A free acid (580 mg, 1.114 mmol) suspended in water (5 mL) was treated with gadolinium acetate (602 mg, 1.48 mmol. 1.33 eq.) in water (3.5 mL) at 65° C. Upon mixing the starting materials the solution became homogeneous but after 25 minutes a pale yellow solid precipitated out; Filtration and washing of the solid with water gave the title product (470 mg).

Analysis calc'd for $C_{22}H_{29}N_6O_9Gd.0.69$ $H_2O$: C, 38.23; H, 4.43; N, 12.16; O, 22.41%. Found: C, 38.34; H, 4.48; N. 12.09; $H_2O$, 1.80%.

EXAMPLE 7

10-[N-(4-Aminophenyl)acetamido]-1,4,7,10-tetraazacyclododecane-1,4,7-triacetic acid, monogadolinium salt

A. 10-[N-(4-Aminophenyl)acetamido]-1,4,7,10-tetraazacyclododecane-1,4,7-triacetic acid, monotriethylammonium salt To a solution of compound A of Example 6 (5.3 g, 10.1 mmol) in water (150 ml) whose pH was adjusted to 7.0 by the addition of 10 N NaOH was added 10% Pd/C catalyst (2.17 g, 1.0 mmol of Pd). The solution was hydrogenated at room temperature under a hydrogen atmosphere (20-25 psi) for 3 hours. The reaction mixture was then filtered to remove the catalyst. The filtrate was concentrated and applied on a 5×20 cm column of anion exchange resin. The column was eluted with a step gradient (5 mM-10 mM) of aqueous triethylammonium bicarbonate solution. The fractions containing the desired compound were combined and concentrated to yield 4.2 g of the title A mono-triethylammonium salt.

Analysis calc'd for $C_{28}H_{49}N_7O_7.1.91$ $H_2O.0.34$ $NCC_2H_5I_3$ C, 54.29; H, 8.78; N, 15.47; ), 21.45%. Found: C, 53-92; H, 9.18; N, 15-58; $H_2O$, 5-45% (H-NMR spectrum supports the presence of 0.34 mol-equivalent of $N(C_2H5)_3$).

B. 10-[N-(4-Aminophenyl)acetamido]-1,4,7,10-tetraazacyclododecane-1,4,7-triacetic acid, monogadolinium salt To a solution of the Compound B of example 6 (3.39 g, 5 mmol) in MeOH (95 ml) and water (18 ml) was added 10% Pd/C catalyst (1.06 g, 0.5 mmol of Pd). The solution was hydrogenated at room temperature under hydrogen atmosphere (20-25 psi) for 10 hours. The solution containing the catalyst was then filtered. After the filtrate was evaporated to dryness, the residue was crystallized from MeOH (30 ml) to give the product (3.04 g).

Analysis calc'd for $C_{22}H_{31}N_6O_7Gd.4.18$ $H_2O$: C, 36.49; H, 5.48; N, 11.61; O, 24.70%. Found: C, 36.22; H, 5.41; N, 11.41; $H_2O$, 10.4%.

EXAMPLE 8

10-[[N-(4-(N'-Isothiocyanto)phenyl]acetamido]]-1,4,7,10-tetraazacyclododecane-1,4,7-triacetic acid, monogadolinium salt This activated species was prepared in situ as follows:

To an aqueous solution (7 ml) of the compound of Example 7.B (194.7 mg, 0.3 mmol) was added thiophosgene (138 mg, 1.2 mmol) in CHCl$_3$ (6 ml). The biphasic mixture was stirred at room temperature until the starting material was consumed completely. The aqueous layer was separated, and its pH (1.3) was adjusted to 5.9 by the addition of 1.0 N NaOH. Mass spectral analysis of the solution showed the presence of a peak at m/e 692 corresponding to Example 8. and

EXAMPLE 9

10-[N-[4-(N'-Methylthioureido)phenyl]acetamido]-1,4,7,10-tetraazacyclododecane-1,4,7-triacetic acid, monogadolinium salt To a solution of the title compound from Example 7 (194.7 mg, 0.3 mmol) in H$_2$O (7.5 ml) was added a solution of thiophosgene (138 mg, 1.2 mmol) in CHCl$_3$ (6 ml). The biphasic mixture was stirred at room temperature until the compound was consumed completely. The aqueous layer (pH 1.0-1.5) was separated, and the CHCl$_3$ layer was washed with water (1 ml×2). The combined aqueous layers were treated with 1 N NaOH to adjust the pH of the so-formed title 8 solution to 6.0. Methylamine (18.04 mg, 0.58 mmol) was then added, and the reaction mixture was stirred for 10 minutes. The resulting solution was loaded on a CHP-20 column and eluted with water and ethanol. The desired title 9 compound was eluted out by 10% of ethanol to give the desired product (129 mg).

Analysis calc'd for C$_{24}$H$_{34}$N$_7$O$_7$SGd.2.99 H$_2$O: C, 37.16; H, 5.19; N, 12.64; O, 20.60%. Found: C, 37.00; H, 5.16; N, 12.39; H$_2$O, 6.94%.

EXAMPLE 10

10-[N-[4-(N',N'-Diethylaminothioureido)phenyl]-acetamido]-1,4,7,10-tetraazacyclododecane-1,4,7-triacetic acid, monogadolinium salt To a solution of the title gadolinium chelate of Example 7 (324 mg, 0.5 mmol) in H$_2$O (15 ml) was added a solution of chiophosgene (230 mg, 2 mmol) in CHCl$_3$ (10 ml). The biphasic mixture was stirred at room temperature until the chelate was consumed completely to provide a solution of the Example 8 isothiocyanato product. The aqueous layer (pH 1.0-1.5) was separated, and the CHCl$_3$ layer was washed with water (2 ml×2). The combined aqueous layers were treated with 1 N NaOH to adjust the pH of the isothiocyanto solution to 6.0. Diethylamine (73.1 mg, 1.0 mmol) was then added, and the reaction mixture was stirred for 10 minutes. The resulting solution was loaded on a CHP 20P column and eluted with water and aqueous ethanol. The desired compound was eluted out by 10% ethanol to give the desired product (286 mg).

Analysis calc'd for C$_{27}$H$_{40}$N$_7$O$_7$SGd 2.31 H$_2$O: C, 40.26; H, 5.58; N, 12.17; O, 18.49%. Found: C, 40.30; H, 5.71; N, 11.99; H$_2$O, 5.16%.

EXAMPLE 11

10,10'[[[[[(1,2-Ethanediyl)diimino]bis(thioxomethyl)-diimino]bis(4,1-phenylene)]diiminobis[1,4,7,10-tetraazacyclododecane-1,4,7-triacetic acid], gadolinium (1:2) salt The Example 8 isothiocyanato derivative solution was prepared as in Examples 8, 9 and 10. Ethylenediamine (11.2 mg, 0.19 mmol) dissolved in water (1.0 mL) was added to this solution. The pH of the resulting mixture was initially increased to 10.04 and then decreased to 7.88 at the end of 3 hours stirring. Concentrated ammonium hydroxide was used to quench the excess Example 8 chelate. The crude product, obtained after removal of the water and ammonium hydroxide, was purified by CHP 20P chromatography. The desired product was eluted out by 10% ethanol to give the dimeric gadolinium chelate (150 mG).

Analysis calc'd for C$_{48}$H$_{66}$N$_{14}$O$_{14}$S$_2$Gd$_2$.2.19 H$_2$O: c, 38.92; H, 4.79; N, 13.24; O, 4.49; S, 4.33%. Found: C, 39.07; H, 4.77; N, 13.19; S, 3.95; H$_2$O, 2.66%.

EXAMPLE 12

10,10'-[[[[(Thioxomethyl)bis(imino)bis(4,1-phenylene)]bis(imino)]bis(2-oxo-2,1-ethanediyl)]-1,4,7,10-tetraazacyclododecane-1,4,7-triacetic acid, gadolinium (1:2) salt The product of Example 7 (194.7 mg, 0.3 mmol) dissolved in water (0.5 ml) was added to the Example 8 isothiocyanato solution described above. The reaction mixture was stirred at room temperature for 10 hours. The resulting solution was applied to a CHP 20P column. The column was eluted with H$_2$O, 2%, 4% and 6% of EtOH containing water in the order mentioned. The desired compound was eluted by 6% of EtOH to give the title product (259 mg).

Analysis calc'd for C$_{45}$H$_{60}$N$_{12}$O$_{14}$SGd$_2$.4.37H$_2$O: C, 38.11; H, 4.88; N, 11.85; O, 20.72, S, 2.2b %. Found: C, 38.35; H, 5.03; N, 11.80; H$_2$O, 5.55%.

EXAMPLE 13

10,10',10"-[[[[[[Iminobis(2,1-ethanediyl)triimino]-tris(thioxomethyl)]-triimino]-tris-(4,1-phenylene)]triimino]tris(2-oxo-2,1-ethanediyl)]tris[1,4,7,10-tetraazacyclododecane-1,4,7-triacetic acid], gadolinium (1:3) salt Tris(2-aminoethyl)amine (19.7 mg, 0.135 mmol) dissolved in water (0.5 mL) was added to the Example 8 isothiocyanato solution described above. The pH of the resulting mixture read 10.10 upon mixing, and then decreased to 7.88 after stirring 18 hours. Concentrated ammonium hydroxide was added to quench the excess Example 8 compound. The crude product, which was obtained after removal of the water and ammonium hydroxide, was purified by CHP 20P chromatography. The desired product was eluted by 20% ethanol to give the trimeric gadolinium chelate (230 mG).

Analysis calc'd for C$_{75}$H$_{105}$N$_{22}$O$_{21}$S$_3$Gd$_3$.6.92H$_2$O: C, 38.44; H, 5.11; N, 13.15; O, 19.0b; S, 4.10%. Found: C, 38.75; H, 5.09; N, 13.14; S, 3.76; H$_2$O, 5.32%.

EXAMPLE 14

10-[2-[[2-(4-Nitrophenyl)ethyl]amino]-2-oxoethyl]-1,4,7,10-tetraazacyclododecane-1,4,7-triacetic acid, monogadolinium salt A. 2-Chloro-N-[2-(4-nitrophenyl)ethyl]acetamide To a solution of p-nitrophenethylamine (hydrochloride salt, 6.0 g, 29.7 mmol) in anhydrous DMA (50 ml) and Et$_3$N (3.0 g, 29.7 mmol) was added chloroacetyl chloride (6.71 g, 59.4 mmol). The reaction mixture was stirred at room temperature for 2 hours. The solvent was removed in vacuo, the residue was dissolved in EtOAc and the solution was washed with aqueous NaHCO$_3$ and brine. The organic layer was dried and the solvent removed to obtain the crude product as a yellow solid. Recrystallization of this material from hot EtOAc/hexanes (10:1) afforded the anilide as a white crystal (5.5 g).

Elemental analysis calc'd C$_{10}$H$_{11}$N$_2$ClO$_3$: C, 49.50; H, 4.57; N, 11.54; Cl, 14.61; O, 19.78%. Found: C, 49.74; H, 4.50; N, 11.12; Cl, 14.35%.

B. 10-[2-[[2-(4-Nitrophenyl)ethyl]amino]-2-oxoethyl-1,4,7,10-tetraazacyclododecane-1,4,7-triacetic acid DO3A sulfate (6.0 g, 13.5 mmol) was dissolved in H$_2$O (100 ml) and the pH of the solution was adjusted to 9.5 by adding 10 N NaOH. To this solution at 80° C. was added a solution of the title A compound (5.5 g, 22.7 mmol) in EtOH (80 ml) over a period of 30 minutes. The pH was maintained at 9.5 by adding 5 N NaOH. The mixture was heated at 80° C. for 48 hours, and the solvents were removed in vacuo. The solid was dissolved in H$_2$O and washed twice with EtOAc. The aqueous layer was evaporated by a water pump at 40° C. to remove traces of EtOAc. The solution was diluted to 600 ml and applied to a 1.5-liter column of anion exchange resin. The column was eluted with a step gradient of aqueous Et$_3$NH$^{+-}$HCO$_3$ solution, 5 mM to 200 mM. The fractions containing the desired compound were combined and concentrated in vacuo. The title B compound (7.67 g) was obtained as the mono triethylammonium salt.

C. 10-[2-[[2-(4-Nitrophenyl)ethyl]amino]-2-oxoethyl]-1,4,7,10-tetraazacyclododecane-1,4,7-triacetic acid, monogadolinium salt The title B compound (monotriethylammonium salt, 65.3 mg, 0.1 mmol) was dissolved in H$_2$O (5 ml) and the pH of the solution adjusted to 4.5 by adding diluted HOAc. To this solution was added a solution of Gd(OAc)$_3$·4H$_2$O (52.8 mg, 0.13 mmol) in H$_2$O (5 ml). The mixture was stirred at room temperature for 1 hour. The solution was then applied to a 400 ml column of CHP-20 resin, using EtOH/H$_2$O (0-15%) as an eluent. The fractions containing the desired compound were combined and removal of the solvent afforded the title compound as a monogadolinium salt (450 mg).

Elemental analysis calc'd for C$_{24}$H$_{33}$N$_6$GdO$_9$·1.93 H$_2$O: C, 38.88; H, 5.01; N, 11.33; Gd, 21.21; O, 23.57%. Found: C, 38.81; H, 5.15; N, 11.40%.

EXAMPLE 15

10-[2-[[3,5-bis[[(2-hydroxyethyl)amino]-carbonyl]phenyl]amino]-2-oxoethyl]-1,4,7,10-tetraazacyclododecane-1,4,7-triacetic acid-gadolinium (III) complex

A. N,N'-bis(2-hydroxyethyl)-5-nitro-1,3-benzenedicarboxamide

A solution containing dimethyl-5-nitroisophthalate (23.9 g, 100 mmol) and ethanolamine (13.4 g, 220 mmol) in methanol (300 mL) was refluxed for 48 hours. The solvent was removed by evaporation under reduced pressure. The crude product was purified by crystallization from EtOAC: MeOH 1 ml v/v) to afford 20.0 g of pure N,N'-bis(2-hydroxyethyl)-5-nitro-1,3-benzenedicarboxamide as white crystals. m.p.=151.3-151.4° C., uncorrected Elemenatal Analysis: Calculated for C$_{12}$H$_{15}$O6N3·0.8 H2O: C, 48.25; H, 5.12; N, 14.07; O, 32.57%.

B. N,N'-bis(2-acetoxyethyl)-5-amino-1,3-benzenedicarboxamide

A solution containing N,N'-bis(2-hydroxyethyl)-5-amino-1,3-benzenedicarboxamide (6.0 g, 20 mmol) and acetic anhydride (11 mL) in pyridine (50 mL) was stirred at room temperature for 4 hours. Water (1 mL) was added to decompose the excess anhydride and the solvent was removed in vacuo. The residue was dissolved in EtOAc (50 mL) and the solution was successively washed with H$_2$O (50 mL), 10% HCl (50 mL), and saturated NaCl solution (50 mL). The aqueous layer was reextracted with EtOAc (50 mL) and the organic layer was combined with the previous extract. The EtOAc layer was dried over MgSO$_4$, filtered, and evaporated to dryness. The residue (7.3 g, 19 mmol) was dissolved in hot MeOH (100 mL) and hydrogenated using cat. 10% Pd/C for 3 hours at 50 psi H$_2$. The filtrate was evaporated to dryness and afforded 6.4 g of pure title B product.

Elemental Analysis Calculated for: C$_{16}$H$_{21}$O$_6$N$_3$: C, 54.70; H, 6.02; N, 11.96; O, 27.32%. Found: C, 54.97; H, 6.19; N, 12.10; ROI, 0.12; H$_2$O, 0.000%.

C. N,N'-bis(2-acetyloxy)ethyl]-5-[(chloroacetyl)amino-1,3-benzenedicarboxamide Chloroacetyl chloride (3 mL) was added dropwise to an ice-cold solution containing N,N'-bis(2-acetoxyethyl)-5-amino-1,3-benzenedicarboxamide (6.4 g, 18 mmol) in anhydrous DMA (5 mL). After one hour, the reaction mixture was neutralized by the addition of saturated aqueous NaHCO$_3$ and the solution was concentrated in vacuo to a syrup. The syrup was dissolved in EtOAc (100 mL) and was successively washed with H$_2$O (2×50 mL) and brine (50 mL). The organic layer was dried over MgSO$_4$, filtered and evaporated to yield 6.2 g of pure title C product.

Elemental Analysis calculated for C$_{18}$H$_{22}$O$_7$N$_3$Cl·0.52 H$_2$O·0.55 CD$_3$OD: C, 48.75; H, 4.85; N, 9.19; Cl, 7.75; O, 24.50%. Found: C, 48.35; H, 5.04; N, 9.30; Cl, 8.20; ROI, 0.00; H$_2$O), 2.16% (desorption KF).

D. 5-[chloroacetyl)amino]-N,N'-bis(2-hydroxyethyl)-5-amino-1,3-benzenedicarboxamide A solution of N,N'-bis(2-(acetyloxy)ethyl]-5-[(chloroacetyl)amino-1,3-benzenedicarboxamide (6.2 g, 14 mmol) in MeOH (20 mL) was treated with NaOMe (600 mg, 10.5 mmol). After 2 hours at room temperature, the mixture was neutralized with AG-50W-X2 (H+ form) resin. The resin was removed by filtration and the solution was evaporated to dryness to afford 4.8 g of crude material. An analytical sample of the title D product was crystallized from MeOH. m.p.=178.4-180.6° C., uncorrected.

Elemental Analysis calcd. for C$_{14}$H$_{18}$O$_5$N$_3$Cl·0.16 H$_2$O: C, 48.51; H, 5.33; N, 12.12; Cl, 10.23; O, 23.81%. Found: C, 48.73; H, 5.45; N, 12.16; Cl, 10.27; ROI, 0.09; H$_2$O, 0.83 (desorption KF).

E. 10-[2-[[3,5-bis[[(2-hydroxyethyl)amino]-carbonyl]phenyl]amino]-2-oxoethyl]-1,4,7,10-tetraazacyclododecane-1,4,7-triacetic acid, monosodium salt A suspension of 5-[chloroacetyl)amino]-N,N'-bis(2-hydroxyethyl)-1,3-benzenedicarboxamide (1.0 g, 2.9 mmol) in water (20 mL) was added to a basic solution (pH 9.8) of DO3A (692 mg, 2.0 mmol) in water (3 mL) maintained at 80° C. A small amount of ethanol (5 mL) was added to during the course of the addition to aid in the solubilization of the chloroanilide. During the course of the reaction, the pH was maintained constant by occasional addition of small aliquots of 10N NaOH. The progress of the reaction was monitored by HPLC. After 20 hours, the reaction was neutralized to pH 6.75 with 1N HCl and applied to a CHP-20 column (150 mL). The product was eluted with water. Fractions containing pure product were combined and evaporated to dryness to afford 1.1 g of the title E product as a white glassy material.

m.p.=176° C. (decomp), uncorrected.

Elemental Analysis calc'd for $C_{28}H_{42}O_{11}N_7Na.1.97\ H_2O$: C, 47.30; H, 6.51; N, 13.79; Na, 3.23; O, 29.17. Found: C, 47.34; H, 6.75; N, 13.45; Na, 2.91; ROI, not determined; $H_2O$, 4.98% (desorption KF).

F. 10-[2-[[3,5-bis[[(2-hydroxyethyl)amino]-carbonyl]phenyl]amino]-2-oxoethyl]-1,4,7,10-tetraazacyclododecane-1,4,7-triacetic acid, monogadolinium salt(VII)

A solution containing the title E ligand (200 mg, 306 µmol) in water (100 µL) was adjusted to pH 4.69 by addition of HOAc. A solution of $Gd(OAc)_3.4\ H_2O$ (187 mg, 461 µmol) in water (50 µL) was added to the ligand and the reaction was stirred for 17 hours at 80° C. The crude product was applied directly onto a CHP-20 column (100 mL). After washing the column with water, the pure product was eluted with 5% EtOH in water. Fractions containing the product were pooled and evaporated to yield 160 mg of pure product.

MS (positive FAB, m/z): $(M+H)^+$ at 809 ($^{158}$Gd).

Elemental Analysis: calc'd for $C_{28}H_{38}O_{11}N_7Gd.2.72\ H_2O$: C, 39.34; H, 5.12; N, 11.4; Gd, 18.39; O, 25.68%. Found: C, 39.41; H, 5.52; N, 11.19; ROI, 17.85; $H_2O$, 5.74% (desorption KF).

EXAMPLE 16

10,10',10'',10''',10'''',10'''''-[[[[[[[(Nitrilo-tri-2,1-ethanediyl)tris(nitrilo)]hexakis-(2,1-ethanediyl)] hexakis(imino)hexakis-(carbonothioyl)]hexakis-(imino)]hexakis-(4,1-phenylene)]hexakis-(imino)]-hexakis-(2-oxo-2,1-ethanediyl)]hexakis[1,4,7,10-tetra-azacyclododecane-1,4,7-triacetic acid], gadolinium (1:6) salt

A. Tris[bis(2-p-toluenesulfonylaminoethyl)-aminoethyl]amine

Tris(2-aminoethyl)amine (0.73 g, 4.96 mmol) and N-tosyl aziridine (5.9 g, 30.0 mmol) were added in 5% aqueous EtOH (10 ml). The reaction mixture was stirred at room temperature. Over a period of 2 hours a white precipitate formed, which made stirring difficult. After another portion of 5% aqueous EtOH (10 ml) was added, the reaction mixture was stirred for 21 hours. The solid was filtered and washed with cold ethanol to obtain the crude product (6.3 g). The crude product was recrystallized twice from hot acetonitrile (120 ml each) to afford the title product, tris[bis(2-p-toluenesulfonylaminoethyl)-aminoethyl]amine (3.4 g) in 52% yield.

HPLC: Retention time 7.7 minutes; YMC $C_8$ basic 120 Å, 4.6×250 mm; 48% acetonitrile in 25 mM HCl; UV at 254 nm; flow rate, 1 ml/min. IR (KBr): 3285, 1599, 1325, 1157, 1094 and 552 cm$^{-1}$. MS(FAB): m/z: 1329.5 $(M+H)^+$; 904 $[M-CH_2N(CH_2CH_2NHTs)_2]$; 438 $[CH_2CH_2N(CH_2CH_2NHTs)_2]$; 424 $[CH_2N(CH_2CH_2NHTs)_2]$.

$^1$H-NMR (DMSO): δ 2.35 (s, 18H, $CH_3$); 2.31, 2.65 (t, 36H, $CH_2$); 7.32-7.67 (m, 24H, benzene ring).

$^{13}$C-NMR (DMSO): 22.05 ($CH_3$); 54.38 ($CH_2$); 127.57, 130.70, 138.75, 143.61 (benzene ring). Anal. Calcd. for $C_{60}H_{84}N_{10}O_{12}S_6.0.18\ H_2O$: C, 54.06; H, 6.38; N, 10.51, S, 14.43. Found: C, 53.95; H, 6.37; N, 10.55; S, 14.29. $H_2O$, 0.25% (desorption Karl-Fisher).

B. Tris[bis(2-aminoethyl)aminoethyl]amine

Tris[bis(2-p-toluenesulfonylaminoethyl)-aminoethyl]amine (1 g, 0.75 mmol) was treated with concentrated $H_2SO_4$ (5 ml) under a $N_2$ atmosphere at 130° C. for 48 hours. After cooling the reaction mixture to 0° C., diethyl ether (40 ml) was added in small portions maintaining the temperature under 10° C. The resulting hygroscopic precipitate was filtered and dissolved in $H_2O$ (5 ml). The solution was basified to pH 13 with 10 N NaOH and extracted with $CH_2Cl_2$. The $CH_2Cl_2$ layer was then dried over $Na_2SO_4$ and concentrated to obtain the title product, tris[bis(2-aminoethyl)aminoethyl]amine (90 mg).

$^1$H-NMR($D_2O$): 2.47-2.68 (t, 36H, $CH_2$). $^{13}$C-NMR ($D_2O$): 37.51 ($CH_2NH_2$); 50.71 ($NCH_2CH_2NH_2$); 55.91 ($NCH_2CH_2N$). MS(FAB): m/z: 427 $(M+NA)^+$; 405 $(M+H)^+$; 288 $[MCH_2N(CH_2CH_2NH_2)_2]^+$; 276 $[MCH_2CH_2N)CH_2CH_2NH_2)_2)_2]^+$.

C. 10,10',10'',10''',10'''',10'''''-[[[[[[[(Nitrilo-tri-2,1-ethanediyl)tris(nitrilo)]hexakis-(2,1-ethanediyl)] hexakis(imino)hexakis-(carbonothioyl)]hexakis-(imino)]hexakis-(4,1-phenylene)]hexakis-(imino)]hexakis-(2-oxo-2,1-ethanediyl)]hexakis[1,4,7,10-tetraazacyclododecane-1,4,7-triacetic acid], gadolinium (1:6) salt Tris[bis(2-aminoethyl)aminoethyl]amine (50 mg, 0.124 mmol) dissolved in water (1.8 ml) was added to Gd(IPA-DO3A) which was prepared as described in the following paragraph (and is also described as the title compound of Example 8 above). The reaction mixture was stirred at room temperature for 20 hours. The reaction mixture was then concentrated to dryness. The residue was dissolved in $H_2O$ (5 ml), and the pH of the resulting solution adjusted to 11.9 by the addition of 1M NaOH. The resulting aqueous solution was applied to a CHP 20 P column (2.5×20 cm). The column was eluted with water and water containing 2%, 5%, 10%, 20% and 25% EtOH in the sequence indicated. The desired compound was eluted out by 25% of EtOH to afford the title compound C (234 mg) as an off-white solid in 46% yield.

$C_{156}H_{222}N_{46}O_{42}S_6.6$ Gd. 23.49 $H_2O$ MW 3606.14 FW 4972.82.

HPLC: Retention time 7.9 minutes; AMP-303 ODS 200 Å, 4.6×250 mm; 16% acetonitrile in 50 mM tris and 10 mM EDTA (pH 7.0); UV at 254 nm; flow rate, 1 ml/min. IR (KBr): 3437, 1618, 1508, 1385, 1317 and 1084 cm$^{-1}$.

MS: m/z: 4550.6 $(M+H)^+$; 2227.7 $(M+2H)^{+2}$. Anal. Calcd. for $C_{156}H_{222}N_{46}O_{42}S_6Gd_6.23.49\ H_2O$: C, 37.68; H, 5.45; N, 12.96, S, 3.87. Found: C, 38.02; H, 5.70; N, 12.83; S, 3.53. $H_2O$, 8.51% (desorption Karl-Fisher).

In situ preparation of Gd(IPA-DO3A): To an aqueous solution (22 ml) of monogadolinium salt of 10-[N-(4-aminophenyl)acetamido]-1,4,7,10-tetraazacyclododecane-1,4,7-tri-acetic acid, Gd(APA-DO3A) (603.3 mg, 0.93 mmol) was added a solution of thiophosgene (427.7 mg, 3.72 mmol) in $CHCl_3$ (18 ml). The biphasic mixture was stirred at room temperature and the progress of the reaction monitored by HPLC using a Nucleosil $C_{18}$ column. When the conversion to the expected product was completed, the aqueous layer was separated, and its pH (1.0) adjusted to 8 by the addition of 1.0 N NaOH.

Abbreviations used herein:
DMA=dimethylacetamide
THF=tetrahydrofuran
MeI=methyl iodide
EtOAc=ethyl acetate
MeOH methanol
EtOH=ethanol
HOAc=acetic acid
Ac=acetyl
DMSO=dimethylsulfoxide
NaOMe=sodium methoxide

What is claimed is:

1. A compound of the formula

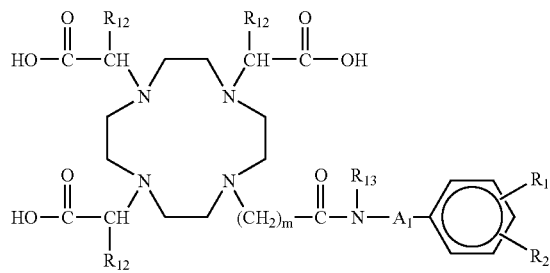

wherein $A_1$ is —$(CH_2)_{m'}$ or a single bond;
$(CH_2)_m$ and $(CH_2)_{m'}$ may independently be substituted with alkyl or hydroxyalkyl;
$R_1$ and $R_2$ are each independently hydrogen or

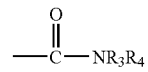

with the proviso that at least one of $R_1$ and $R_2$ must be other than hydrogen;
$R_3$ and $R_4$ are independently hydrogen, alkyl, arylalkyl, aryl, alkoxy and hydroxyalkyl;
$R_{12}$ is hydrogen, alkyl or hydroxyalkyl;
$R_{13}$ is hydrogen, alkyl, arylalkyl, aryl, alkoxy or hydroxyalkyl;
m and m' are independently 1 to 5; and multimeric forms thereof.

2. The compound of claim 1 having the name 10-[2-[[3,5-Bis-[[(2-hydroxy-1-(hydroxymethyl)ethyl]amino]carbonyl]phenylamino]2-oxoethyl]1,4,7,10-tetraazacyclododecane-1,4,7-triacetic acid.

3. The gadolinium complex of the compound of claim 2.

4. The compound of claim 1 having the name 10-[2-[[3,5-Bis[[(2-methylbutyl)amino]carbonyl]-phenyl]amino]2-oxoethyl]1,4,7,10-tetraazacyclo-dodecane-1,4,7-triacetic acid.

5. The gadolinium complex of the compound of claim 4.

* * * * *